US009047439B2

(12) United States Patent
Hershkowitz et al.

(10) Patent No.: US 9,047,439 B2
(45) Date of Patent: Jun. 2, 2015

(54) REACTOR WITH REACTOR HEAD AND INTEGRATED VALVE

(71) Applicant: ExxonMobil Chemical Patents Inc., Baytown, TX (US)

(72) Inventors: Frank Hershkowitz, Basking Ridge, NJ (US); Richard John Basile, Rockaway, NJ (US); Jeffrey William Frederick, Centreville, VA (US); John William Fulton, Annandale, VA (US); Paul F. Keusenkothen, Houston, TX (US); Bryan A. Patel, Arlington, VA (US); Andrew Richard Szafran, Leauge City, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 13/957,488

(22) Filed: Aug. 2, 2013

(65) Prior Publication Data
US 2013/0317801 A1 Nov. 28, 2013

Related U.S. Application Data

(62) Division of application No. 13/102,641, filed on May 6, 2011, now Pat. No. 8,524,159.

(60) Provisional application No. 61/349,464, filed on May 28, 2010.

(51) Int. Cl.
*G05B 15/02* (2006.01)
*G06F 19/00* (2011.01)
(Continued)

(52) U.S. Cl.
CPC ............ *G06F 19/709* (2013.01); *B01J 8/0453* (2013.01); *B01J 8/048* (2013.01); *B01J 8/0484* (2013.01);
(Continued)

(58) Field of Classification Search
CPC ............ B01J 19/00; B01J 19/18; B01J 19/24; B01J 19/32; B01J 7/00; B01J 8/00; B01J 12/007; G05B 11/00; G05B 11/01; G05B 13/00; G05B 13/02; G05B 15/00; G05B 15/02; G05B 17/00; G05B 17/02; G05B 19/00; G05B 19/02; G05B 19/04; G05B 19/042; G05B 19/0423; G05D 3/00; G05D 7/00; G05D 7/09; G05D 7/0617; G05D 7/0629; G05D 7/0635; G05D 27/00; G05D 27/02
USPC ............ 422/105, 114, 115, 129; 702/85, 100; 700/90, 275, 282
See application file for complete search history.

(56) References Cited

U.S. PATENT DOCUMENTS 1,543,909 A  6/1925 Dyrssen
2,257,178 A  9/1941 Martin et al.
(Continued)

FOREIGN PATENT DOCUMENTS

JP    280921    10/1999
JP  11280921    10/1999
PL  175716 B1 *  1/1999

OTHER PUBLICATIONS

Machine translation of JP 11-280921A, which was published on Oct. 15, 1999.

*Primary Examiner* — Natasha Young

(57) ABSTRACT

A reactor with minimal dead volume especially suited to reverse-flow applications comprises: a) a reactor body; b) a first head engaged with said reactor body; c) a first conduit extending from outside said head to at least partially through said head; and d) a first valve in flow communication with said first conduit controlling fluid flow along a flow path extending from the first valve and through the reactor body. The reactor is especially suited for use in a process for rapid stream-switching of at least two streams in a reverse-flow reactor.

6 Claims, 4 Drawing Sheets

(51) Int. Cl.
  B01J 8/04 (2006.01)
  C01B 3/46 (2006.01)
  C10G 9/26 (2006.01)
  G05B 15/00 (2006.01)
  G05B 19/00 (2006.01)
  G05B 19/02 (2006.01)
  G05B 19/04 (2006.01)
  G05B 19/042 (2006.01)
  G05D 3/00 (2006.01)
  G05D 7/00 (2006.01)
  G05D 7/06 (2006.01)
  G05D 27/00 (2006.01)
  G05D 27/02 (2006.01)
  B01J 8/00 (2006.01)
  B01J 19/00 (2006.01)

(52) U.S. Cl.
  CPC .............. B01J 8/0492 (2013.01); C01B 3/46 (2013.01); C01B 2203/0216 (2013.01); C01B 2203/0233 (2013.01); C01B 2203/0238 (2013.01); C01B 2203/0266 (2013.01); C10G 9/26 (2013.01)

(56) References Cited

U.S. PATENT DOCUMENTS

| | | |
|---|---|---|
| 2,438,467 A | 3/1948 | Tyson et al. |
| 2,556,835 A | 6/1951 | Barr |
| 3,014,861 A | 12/1961 | Buningh |
| 4,222,875 A | 9/1980 | Sikula, Jr. |
| 4,541,995 A | 9/1985 | Kim et al. |
| 4,834,038 A | 5/1989 | Montagni |
| 5,177,988 A | 1/1993 | Bushnell |
| 5,212,948 A | 5/1993 | Gillingham et al. |
| 5,833,938 A | 11/1998 | Blazejewski |
| 5,837,205 A | 11/1998 | Bayer et al. |
| 5,871,349 A | 2/1999 | Johnson et al. |
| 6,039,927 A | 3/2000 | Greco |
| 6,086,828 A | 7/2000 | Thompson |
| 6,129,139 A | 10/2000 | De Clerc |
| 6,213,758 B1 | 4/2001 | Tesar et al. |
| 6,261,092 B1 | 7/2001 | Cash |
| 6,321,462 B1 | 11/2001 | Seidl et al. |
| 6,336,278 B1 | 1/2002 | Crawford et al. |
| 6,443,111 B1 * | 9/2002 | LaDow .................... 123/90.11 |
| 6,576,198 B2 | 6/2003 | Cash |
| 6,669,472 B1 | 12/2003 | Cash et al. |
| 6,749,815 B2 | 6/2004 | Cash |
| 6,899,121 B2 | 5/2005 | Cash |
| 6,978,977 B2 | 12/2005 | Cash et al. |
| 7,150,446 B1 | 12/2006 | Cash et al. |
| 7,325,562 B2 | 2/2008 | Cash |
| 7,398,645 B2 * | 7/2008 | Zheng et al. .................... 60/288 |
| 7,491,250 B2 | 2/2009 | Hershkowitz et al. |
| 7,766,025 B2 | 8/2010 | Greco |
| 7,815,873 B2 | 10/2010 | Sankaranarayanan et al. |
| 7,846,401 B2 | 12/2010 | Hershkowitz et al. |
| 7,914,667 B2 | 3/2011 | Keusenkothen et al. |
| 7,943,808 B2 | 5/2011 | Hershkowitz et al. |
| 7,976,797 B2 | 7/2011 | Chun et al. |
| 2001/0044090 A1 | 11/2001 | Cash |
| 2003/0221725 A1 | 12/2003 | Greco |
| 2004/0086822 A1 | 5/2004 | Cash et al. |
| 2005/0112038 A1 | 5/2005 | Stoll et al. |
| 2006/0188760 A1 | 8/2006 | Hershkowitz et al. |
| 2008/0142409 A1 | 6/2008 | Sankaranarayanan et al. |
| 2008/0300438 A1 | 12/2008 | Keusenkothen et al. |
| 2008/0314550 A1 | 12/2008 | Greco |
| 2010/0126907 A1 | 5/2010 | Hershkowitz et al. |
| 2010/0130803 A1 | 5/2010 | Keusenkothen et al. |
| 2010/0288617 A1 | 11/2010 | Hershkowitz et al. |
| 2010/0290978 A1 | 11/2010 | Chun et al. |
| 2010/0292522 A1 | 11/2010 | Chun et al. |
| 2010/0292523 A1 | 11/2010 | Hershkowitz et al. |
| 2011/0008226 A1 | 1/2011 | Hershkowitz et al. |
| 2011/0009681 A1 | 1/2011 | Hershkowitz et al. |
| 2011/0011768 A1 | 1/2011 | Keusenkothen |

* cited by examiner

REACTOR WITH REACTOR HEAD AND INTEGRATED VALVE

RELATED PRIORITY APPLICATIONS

This application is a divisional of U.S. application Ser. No. 13/102,641, filed May 6, 2011, now allowed, which claims benefit of and priority to U.S. Ser. No. 61/349,464, filed May 28, 2010, the disclosures of which are incorporated by reference in their entireties.

FIELD

The present invention relates to a reactor, e.g., reverse-flow reactor, whose configuration includes a valve associated with the reactor head which minimizes dead volume between the valve and reactor bed and provides for a durable valve arrangement. The present invention also relates broadly to a process for using such a reactor.

BACKGROUND

Reverse-flow reactors (RFRs) are known in the art, for example, Wulff pyrolysis and regenerative reactor and other regenerative reactors, including regenerative thermal oxidizers (RTO). These reactors are typically used to execute cyclic, batch-generation, high temperature chemistry. Regenerative reactor cycles are either symmetric (same chemistry or reaction in both directions) or asymmetric (chemistry or reaction changes with step in cycle). Symmetric cycles are typically used for relatively mild exothermic chemistry, examples being regenerative thermal oxidation (RTO) and autothermal reforming (ATR). Asymmetric cycles are typically used to execute endothermic chemistry, and the desired endothermic chemistry is paired with a different chemistry that is exothermic (typically combustion) to provide heat of reaction for the endothermic reaction. Examples of asymmetric cycles are Wulff pyrolysis processes and pressure swing reforming processes (PSR).

To operate the RFRs, various operational features should be considered. For instance, one feature of RFRs is a gas hourly space velocity, which is the space velocity of a gas over a given reactor volume. Typically, a high gas hourly space velocity (and hence reactor productivity) has a small reactor cycle time, while low has hourly space velocity has a longer reactor cycle time. For pyrolysis processes using a RFR, high velocities are needed to achieve short residence times that facilitate conversion to preferred products. A second feature is that the volume of gas remaining in the RFR at the end of one cycle (void volume) should be managed, e.g., swept out, before the beginning of the next cycle, which gas-volume management may result in inefficiency and additional costs. A third feature is that bed structures (packing) needed to provide rapid heat transfer (for sharp thermal gradients and resulting high efficiency) also results in high pressure drop. Thus, the RFR design should consider space velocity, void volume, and packing properties to properly manage the system. Accordingly, certain drawbacks in conventional RFRs, such as properties of conventional packing and long cycle times, have prevented these reactors from being broadly used in the energy and petrochemical fields.

RFRs have historically utilized different packing material in the bed structures. Typically, these reverse-flow reactors utilize checker brick, pebble beds or other available packing. This type of bed structure typically has low geometric surface area ($a_V$), which minimizes pressure drop per unit of reactor length, but also reduces volumetric heat transfer rate. One basic principle of an asymmetric reverse flow reactor is that heat is stored in one step and is used to accomplish a desired endothermic chemistry in a second step. Thus, the amount of desired chemistry that can be achieved, per volume of reactor, is directly related to the volumetric heat transfer rate. Lower heat transfer rates thereby require larger reactor volumes to achieve the same amount of desired chemical production. Lower heat transfer rates may inadequately capture heat from RFR streams, leading to greater sensible heat loss and consequently lower efficiency. Lower heat transfer rates may also lead to longer cycle times, as the stored heat is used more slowly, and therefore lasts longer for a given bed temperature specification. Historic RFR's, with low-$a_V$ checker-brick or pebble bed packing, are larger (e.g., longer and more capital intensive) and have cycle times of two minutes or greater. As such, these reactors limit reactor efficiency and practical reactor size.

As an enhancement, some RFRs may utilize engineered packing within the bed structure. The engineering packing may include a material provided in a specific configuration, such as a honeycomb, ceramic foams or the like. These engineered packings have a higher geometric surface area ($a_V$), as compared to other bed structures. The use of this type of packing allows for higher gas hourly space velocity, higher volumetric reactor productivity, higher thermal efficiency, and smaller, more economical reactors. However, these more-economical reactors use heat more rapidly and thus may require reduced cycle times. Pressure swing reforming processes (PSR) are an example of such a preferred RFR.

Further, as a result of using this type of packing material, the size of the reactor may be reduced, which provides significant capital cost savings. However, adjusting the packing material of the reactors impacts other operational features. For instance, the increase in volumetric surface area ($a_V$) is typically accomplished using smaller flow channels that result in higher pressure drop per unit of reactor length. To compensate for this, these enhanced RFR's are configured to have short lengths. When applied to large petrochemical applications, diameter is increased to enable high productivity, but length is limited by pressure drop, thus leading to a high ratio for diameter per length (D/L). Conventional reactor designs typically collect fluids emerging from a bed and duct those fluids to some external valve. The volume of such ducting is in some proportion to the reactor diameter, because the ducting needs to collect gas from the entire diameter. Thus, for a conventional reactor having a high D/L ratio, the volume of ducting can be very large compared to the volume inside the bed. Use of a conventional reactor design for an enhanced RFR thus results in large void volumes (primarily in the ducting), which creates problems for gas volume management.

Unfortunately, conventional reactor valve systems have certain limitations that do not operate properly for enhanced, high-productivity reactors (e.g., compact reactors employing short cycle times). For instance, conventional reactor valve systems typically fail to meet the durability requirements of RFRs and may not handle the short cycle times. Petrochemical valves can have maximum cycle lifetimes on the order of 500,000 cycles, is which correspond to less than one year of operation—inadequate for petrochemical use involving rapid cycle times. In addition, conventional valves are placed outside the reactor and use manifolding to carry gases between the bed and the valve, while providing uniform flow distribution across the bed. Given the wide and short beds of RFRs, this manifolding holds a large gas volume that has to be managed on every cycle change.

As an example, Japanese Patent Application No. 280,921/ 1999 to Taga discloses a high-temperature heat exchanger with a plurality of high-temperature gas switching poppet valve pairs which control the flow of high-temperature preheated air and high-temperature waste gas over a regenerative heat exchange element.

U.S. Patent Application Publication No. 2009/0008292 to Keusenkothen et al. discloses pyrolyzing hydrocarbons in a reverse-flow type regenerative pyrolysis reactor system.

U.S. Pat. No. 7,491,250 to Hershkowitz et al. discloses production of synthesis gas through a cyclic, packed-bed operation which includes reforming by preheating a first zone, introducing a hydrocarbon-containing feed with steam through the first zone inlet, and reforming over a catalyst in the first zone to form synthesis gas which is passed to a second zone where it is cooled.

U.S. Patent Application Publication No. 2007/0144940 to Hershkowitz et al. and U.S. Patent Application Publication No. 2008/0142409 to Sankaranarayanan et al. teach a regenerative bed reverse flow reactor wherein the location of the exothermic reaction is controlled. The regenerative reactor bed is regenerated by supplying a first reactant through a first channel to a first regenerative bed and a second reactant through a second channel in the first regenerative bed, combining first and second reactants in a gas mixer, and reacting to produce a heated reaction product which is passed through a second regenerative bed to transfer heat thereto.

U.S. Patent Application Publication No. 2009/008292 to Keusenkothen et al. teaches pyrolyzing hydrocarbons containing non-volatiles in a regenerative pyrolysis reactor system. Feedstock is heated to provide a vapor phase which is fed to the pyrolysis reactor system and converted to form a pyrolysis product.

U.S. Patent Application Publication No. 2008/0314550 to Greco teaches a regenerative heat exchanger that uses inlet and outlet poppet valves which are operated in tandem and located outside the head space of the heat exchanger.

Accordingly, it is desirable to provide a reverse-flow reactor system that is minimizes dead volumes between its valves and reactor beds, while providing extended valve lifetimes to millions of cycles, in rugged, high-temperature conditions at the reactor inlet and outlet. Further, there is a need for an enhanced method and apparatus to implement an industrial-scale, high-GHSV RFR's, which has valves that enhance the cycle time of RFRs and manage the purging of fluid between cycles. The present techniques provide a method and apparatus that overcome one or more of the deficiencies discussed above.

SUMMARY

In a first aspect, the present invention relates to a reactor comprising: a) a reactor body; b) a first head engaged with said reactor body; c) a first conduit extending from outside said head to at least partially through said head; and d) a first valve in flow communication with said first conduit controlling fluid flow along a flow path extending from the first valve and through the reactor body. For present purposes, "flow path" may be characterized as the total volume through which fluid passes, including an open flow path. For present purposes, a "head" may be a dished head, meaning it is of substantially concave shape internally, e.g., it can be substantially round, substantially elliptical, substantially torispherical, or substantially hemispherical.

In a second aspect, the present invention relates to a reactor comprising: a) a reactor body partially enclosing a reaction and/or heat exchange region comprising two substantially opposing open ends; b) a first head capping one end of the reactor body; c) a second head capping the opposing end of the reactor body; d) a fixed bed comprising a region proximal to the first head, a region proximal to the second head and a central region disposed therebetween, which fixed bed is disposed within the reactor body and comprises solid material capable of promoting heat exchange and/or reaction of a gas stream; e) at least one gas stream inlet associated with the first head opening a pathway through the first head and into the reactor body and at least one gas stream outlet associated with the second head opening a pathway from the reactor body and through the second head; f) at least one inlet poppet valve controlling the gas stream inlet and integrated with the head associated with the inlet, the inlet poppet valve comprising a linearly actuatable valve stem; g) at least one outlet poppet valve controlling the gas stream outlet and integrated with the head associated with the outlet, the outlet poppet valve comprising a linearly actuatable valve stem; and h) at least one actuator engageable with the linearly actuatable valve stem of f) and/or g) providing valve opening and closing by imparting linear motion to the poppet valve to allow gases to pass from outside the reactor to inside the reactor body, and from inside the reactor body to is outside the reactor so as to provide changeable flow operation.

In a third aspect, the present invention relates to a process for rapid stream-switching of at least two streams in a reverse-flow reactor comprising a reactor body partially enclosing a reaction and/or heat exchange region comprising two substantially opposing open ends with a first head capping one end of the reactor body, a second head capping the opposing end of the reactor body, a fixed bed disposed within the reactor body comprising solid material capable of promoting heat exchange and/or reaction of a gas stream. The process comprises: i) introducing from one or more inlet gas sources at least one first gas stream to at least one gas stream inlet associated with the first head through the first head and into the reactor body and withdrawing a treated first gas stream from the reactor body and through the second head to at least one gas stream outlet associated with the second head; wherein said introducing and withdrawing are controlled respectively by at least one intake poppet valve located in the first head and at least one exhaust poppet valve located in the second head; and ii) introducing from one or more inlet gas sources at least one second gas stream to at least one gas stream inlet associated with the second head through the second head and into the reactor body and withdrawing a treated second gas stream from the reactor body and through the first head to at least one gas stream outlet associated with the first head, wherein said introducing and withdrawing are controlled respectively by at least one intake poppet valve or other intake flow control means located in the second head and at least one exhaust poppet valve located in the first head.

DETAILED DESCRIPTION

Figure 1:
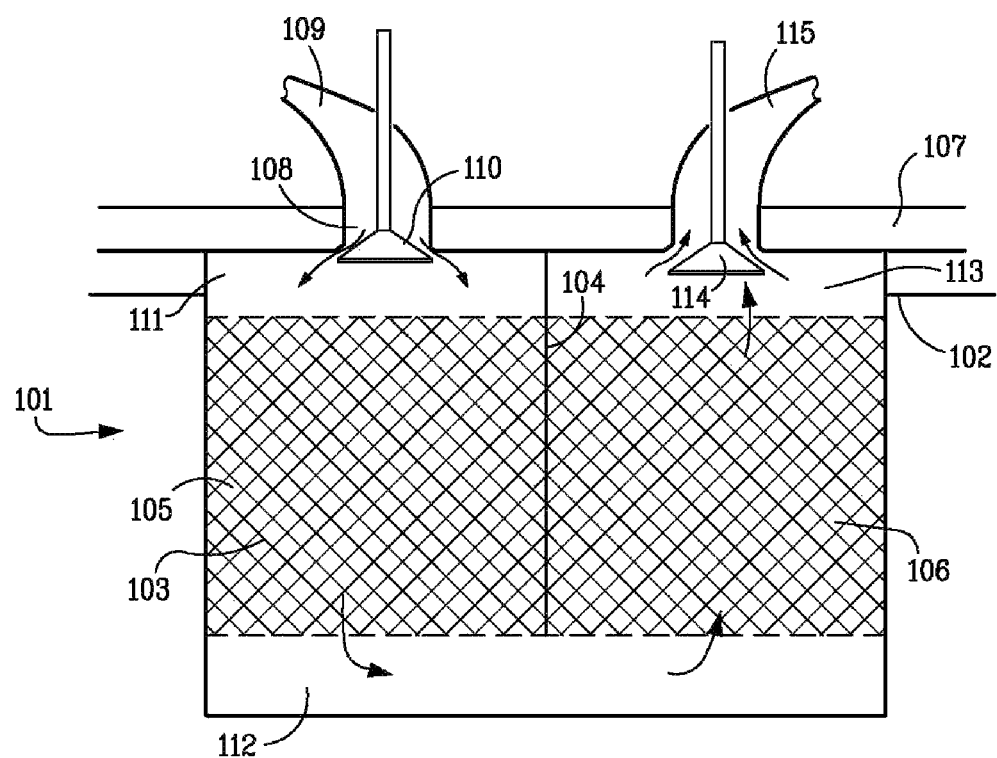
FIG. 1 is an illustration of an asymmetric reverse flow reactor with a single head and associated valve assembly according to an embodiment of the present invention.

The present inventors have discovered that a reverse-flow reactor system having reduced open flow path volume between the valves and reactor beds with extended valve life even under high-temperature conditions may be achieved by a reactor configuration or design that substantially integrates valves into a reactor head. Such a design can enable the introduction and removal of overall large flow volumes with minimum pressure drop and low dead volume, and with substantially uniform flow distribution. For present purposes, open flow path volume corresponds to the volume outside of the reactor beds that effect the gas treating or the reactor, along the flow path between the valves and the reactor/heat exchanger bed. This open flow path volume contributes little to the treatment of gases in the reactor, but may hold large volumes of gases that should be managed with every reversal of flow direction in the operating cycle of the reactor, either by accommodating gases of one step in the product stream of the opposing step, or by providing a means and/or fluids to sweep this gas out of the reactor in between steps of opposing flow direction. The design of the present reverse-flow reactor uses one or more valves, e.g., poppet valves—typically comprising a disk element that modifies the opening controlled by the valve, and a stem element on which an actuating means may operate—for each process stream. As may be appreciated, the poppet valve may include other elements that perform essentially similar function to the disk element, such as other geometric shapes (e.g., elliptical or a hemispherical shapes) or different profiles depending on a specific configuration. Each of the valves may be located substantially within the reactor head. Multiple valves can be used for large diameter heads with manifolding outside the valves to carry feeds and products to and from the valves.

Reverse-flow reactors, and even regenerative heat exchangers, typically perform some treatment to the gases that pass through. When flow is reversed, regions near an inlet become regions near an outlet, and gas compositions or conditions that are typical of inlet conditions for one step are suddenly proximate to, and even flow into, the outlet of the subsequent step. For asymmetric reverse-flow reactors, gasses in alternate steps may be very different. Impurities in one step may be inappropriate for the next. For example, in steam reforming a regeneration stream may be composed mostly of nitrogen, while reforming streams may be composed mostly of hydrogen, and residual oxygen from regeneration may be problematic as a contaminant in the reforming product hydrogen. The extent of this contamination problem is minimized in the present techniques by providing a reactor that minimizes the volume of gasses that remain in the reactor at the end of a step. Additional steps may be taken to mitigate the extent or impact of gas carryover. The reactor may be purged at the end of one step to eliminate problematic components. In the above-mentioned steam reforming example, inert gas may be introduced into the reactor to sweep residual oxygen out before beginning hydrogen manufacture. Purging gases may be introduced using additional sets of the poppet valves described in this application, or may be introduced via more conventional means, such as conduits passing through the heads with more conventional process valves and manifolds located outside the head. Achieving high uniformity of bed velocity, as described herein, may be less important for purging streams than for reacting streams because there is reduced expectation of treating these purging streams. Alternatively, accommodation may be made in post-reactor processing for contaminants that arise due to cycling. For example, hydrocarbon that remains in the reactor after a steam reforming step may be managed as a combustion product contaminant by means of a catalytic converter in the flue gas to burn out remaining fuel. The magnitude of post reactor treatments, and/or the magnitude of purging requirements is minimized by use of a reactor, as disclosed herein, that minimizes unnecessary gas volumes residing within the reactor.

In a first aspect, as earlier noted, the present invention relates to a reactor comprising: a) a reactor body; b) a first head engaged with said reactor body; c) a first conduit extending from outside said head to at least partially through said head; and d) a first valve in flow communication with said first conduit controlling fluid flow along a flow path extending from the first valve and through the reactor body. In certain embodiments, the term "conduit" describes those portions of the reactor which can provide a path for fluid flow from a location outside the reactor body and through at least a portion of the head or a valve seat associated with the head, toward the reactor body. In some embodiments, a conduit extends completely through the head and into the reactor body. In certain embodiments, a conduit can include manifolds or other portions of the reactor that guide fluid flow from outside the reactor body towards the reactor body. For present purposes, "flow path" can be characterized as the space within the reactor through which reactants and/or products flow. The volume of the flow path typically consists of i) a packed flow path volume (further characterized below) within a solids-fluids contact portion of the reactor bed and ii) an open flow path volume (further characterized below) between the valve(s) and the reactor bed, as well as any open flow portion within the reactor bed. Typically, a reactant or products fluid flows into the reactor through a controlling inlet valve and out of the reactor through a controlling outlet valve. As the fluid traverses between inlet and outlet valves, it travels through regions where there is substantial contact with reactor contents (called packed flow path volume) and regions where there is little contact with reactor bed contents (called open flow path volumes). The sum of pathways within the reactor volume that are accessible to the flowing fluid as it passes from inlet valve to outlet valve are considered herein to be the fluid "flow path", and it comprises both packed and open reactor volumes. Typically, these two volumes sum to the total reactor volume available for flow that is in between the valves that are on opposing ends of the flow path and are controlling fluid flow along the flow path. Conveniently, such volumes are measured and calculated with valves in closed positions. Volumes of insulating materials at the perimeter of the reactor vessel are typically not considered to be part of either flow path volume because it is not expected that any substantial flow travel through the insulation. Volumes are computed on a bulk basis, to include solids and void spaces within reactor components, as long as solids are reasonably proximate to fluid flow paths, preferably at a distance less than 2 centimeter (cm) from a fluid flow path.

In some embodiments of the invention, the reactor further comprises at least one of: e) a second head engaged with said reactor body; f) a second conduit extending from outside the first head or the second head to at least partially through said respective head; and g) a second valve in flow communication with said second conduit controlling fluid flow along the flow path including a portion extended from the reactor body to the second valve.

In some embodiments, the first valve has a substantially open position when fluid flow in the flow path is in a first flow direction and a substantially closed position when fluid flow in the flow path is in a second, opposite flow direction. The reactor can have a first valve pair on opposite sides of at least a portion of the flow path, wherein said first valve and second valve are each in a substantially open position when fluid flow in the flow path is in a first flow direction and a substantially closed position when fluid flow in the flow path is in a second, opposite flow direction.

In some embodiments, the reactor further comprises: h) a third conduit extending from outside the first head or the second head to at least partially through said respective head; i) a third valve in flow communication with said third conduit controlling fluid flow along the flow path including a portion extended from the reactor body to the third valve; j) a fourth conduit extending from outside the first head or the second head to at least partially through said respective head; and k) a fourth valve in flow communication with said second conduit controlling fluid flow along the flow path including a portion extended from the reactor body to the fourth valve. The reactor can have a second valve pair comprising said third valve and said fourth valve on opposite sides of at least a portion of the flow path, controlling flow in the second, opposite flow direction wherein the third valve and the fourth valve are each in a substantially closed position when the fluid flow in the flow path is in the first flow direction and in a substantially open position when fluid flow in the flow path is in the second, opposite flow direction.

In certain embodiments, the reactor is a regenerative reactor capable of operating with regenerative reactor cycles which are symmetric, i.e., with the same chemistry or reaction in both directions. Symmetric cycles are typically used for relatively mild exothermic chemistry, examples being regenerative thermal oxidation (RTO) and autothermal reforming (ATR).

In other embodiments, the reactor is a regenerative reactor capable of operating with regenerative cycles which are asymmetric, i.e., an asymmetric reverse flow reactor, in which the chemistry or reaction changes according to each step in the cycle, or directional flow. Asymmetric cycles may be used to execute endothermic chemistry, and the desired endothermic chemistry is paired with a different chemistry that is exothermic (typically combustion) to provide heat of reaction for the endothermic reaction. Examples of asymmetric cycles are Wulff cracking processes and pressure swing reforming processes (PSR). An asymmetric reverse flow reactor typically has an inlet for forward flow that is supplied by a reactant, which is different than that provided by an inlet for the reverse flow. For example, Pressure-Swing Reforming (PSR) is a process which provides an oxidizing gas as one of its reactants in an inlet for forward flow and a hydrocarbon-steam gas mixture as a second reactant supplying an inlet for reverse flow of the reactor. More than one reactant may be introduced in the forward flow direction to provide a combined forward flow, as well as a different combination of reactants in the reverse flow direction to provide a combined reversed flow. In any event, asymmetric reverse flow reactor requires that the combined forward flow and combined reverse flow differ in composition.

In other embodiments, the reactor comprises one or more additional valves, each in flow communication with one of said first, second, third, or fourth conduits via an additional conduit extending at least partially through said additional conduit's respective head, operating in phase with any other valves in fluid communication with said additional conduit and controlling fluid flow along the flow path including a portion extended from the reactor body to the respective valve. In these embodiments, the term "in flow communication with" or "in fluid communication with" means in direct flow communication, i.e., without intervening valves or other closure means for obstructing flow, and also means flow communication within the head or attached manifolds, i.e., not in fluid communication by means of the reactor flow path. Such embodiments include those where an additional conduit carrying fluid to its associated valves is located entirely within its head. For example, a conduit comes into a head from outside the head (as a primary conduit) and branches into one or more "additional conduits" (or secondary conduits) extending to different valves which control flow from the conduits through the valves to a flow path directed through the reactor body. The same flow path can be used by flows in both the forward and reverse directions, the direction depending on which valves in the reactor are open and which valves are closed. For present purposes, an "additional conduit" can be a primary conduit or a secondary conduit, depending on the particular reactor design. Thus, in some embodiments two neighboring valves (typically within the same head) carry the same reactant or gas stream and operate in phase.

The term "operate in phase" as used here and elsewhere throughout the present specification relates to two or more inlet valves or two or more outlet valves opening and closing substantially together, say, with at least 80% overlap, say at least 90% overlap (with 100% overlap being identical or completely in phase). For example, considering the time interval during which a valve is in a certain state, i.e. open or closed, at least 80%, say at least 90% of that time interval is common to all valves that are "in phase." In other embodiments, tolerances on valve phasing are tighter to enable the allowance of less time in between valve changes. In such embodiments, considering the time interval during which a valve is changing state, i.e., opening or closing, at least 80%, preferably at least 90% of that time interval is common to all valves that are "in phase." In certain embodiments of the present techniques, valves that are in phase may have a range of time to begin the travel from open to close. As an example, the first valve may begin opening at time 0 and the final valve in the same phase may begin opening at some time in the future $t_0$ (typically a small fraction of the valve open time or in some embodiments of the valve opening time) and still has the same fluid flow composition and direction. Valves that are in phase may or may not open to the same lift height. For valves that are in phase, the height from the valve with the highest lift height to the valve with the lowest lift height, the lowest lift height may be down to 20% or even 50% of lift height of the valve with the highest lift height.

The first conduit may pierce the upper external surface of the head, while the "additional conduit" can be contained entirely within the head, although the actuation mechanism of the additional conduit's associated valve can, in some embodiments, pierce the head in which it resides. Alternately, this associated valve can be actuated by the same mechanism that activates the primary conduit's associated valve. During operation, these embodiments of the reactor typically comprise four basic primary conduits for: forward flow inlet (or intake), forward flow outlet (or exhaust), reverse flow inlet (or intake), and reverse flow outlet (or exhaust), with at least one valve being associated with each. In some embodiments, more than one valve can be associated with at least one of the basic conduits. An additional valve increases the capacity of the conduit with which it is associated. Typically, valves associated with a particular primary conduit or its associated secondary conduit are operated together substantially in phase to provide a flow in one direction along a specific flow path. Certain embodiments of the reactor utilize only primary conduits, extending outside the head, with no secondary conduits present. This improves ease of servicing the associated valves which are accessible from outside the reactor.

In certain embodiments of the reactor, the reactor body comprises a reactor bed, and the volume of the flow path consists of i) a packed flow path volume within a solids-fluids contact portion of the reactor bed and ii) an open flow path volume between the valve(s) and the reactor bed, as well as any open flow portion within the reactor bed. Typically, the packed flow path volume comprises the volume in the reactor bed that is at a distance less than 2 cm from a solids-fluid contact surface, preferably less than 1 cm from a solids-fluid contact surface. Defined as such, the packed flow path volume includes both solid and fluid volume along the flow path. Typically, it represents the bulk volume of the region of a reactor bed containing bed packing and through which the fluids are flowing. The solids-fluids contact portion of the reactor bed typically has a wetted area greater than $0.5\ cm^2/cm^3$ in all regions of said portion of the reactor bed. The term "wetted area" as used herein represents the area of fluid/solid boundaries within a unit volume, divided by that unit volume. As used in the present disclosure, "wetted" simply means an interface between fluid and solid and is not meant to imply contact with a specific fluid such as water. The wetted area is also known in the art as packing surface area, and sometimes as geometric surface area, and is understood in the art to include fluid/solid boundaries in channels that are relevant to bulk flow through the bed. As such, wetted area typically does not include area within any micro pores that might be within packing or channel walls. In some embodiments, the ratio of the open flow path volume to packed flow path volume is less than 1, preferably, is less than 0.5. Packed flow path volume is typically measured by calculating that volume in the flow path wherein solids-fluids contact occurs as a fluid passes through the reactor body. Open flow path volume constitutes the remainder of volume in the flow path of the reactor body and can include not only those spaces in the reactor body above and below a reactor bed, but also regions within the reactor bed wherein solids-fluids contact does not occur, e.g., mixing zones or any other zones within the reactor bed which lack surfaces providing intimate solids contact with the flowing fluids along the flow path. As a matter of convenience, open flow path volume is typically computed with all valves in their closed positions.

In some embodiments, the reactor bed comprises a fixed bed core comprising solid material capable of heat exchange. Such solid materials are selected to be durable against the physical and chemical conditions within the reactor and can include metallic, ceramic, or other, depending on the type of reaction intended. For example, a lower-temperature steam reforming or steam cracking application may use metal or silica-alumina materials, while a higher-temperature pyrolysis reactor can use high-purity alumina components. The structure of the reactor bed can include a central mixing zone including mixing means, e.g., those of the reactor bed described in U.S. Published Patent Application Publication No. 2007/0144940, incorporated herein by reference. In certain embodiments, at least one of the valves is a poppet valve comprising a disk element connected to a valve stem element. The poppet valve disk element typically has a surface facing the proximal reactor bed surface, similar to those encountered in internal combustion engines. The surface of the disk element can be substantially round, for seating in a substantially round opening. For present purposes, the term "substantially round" can include ellipsoidal shapes such as those found in certain high performance engines. This surface can also be flat or profiled. In certain embodiments wherein the poppet valve disk element may have a surface that is profiled inward or outwardly relative to the opening on which it operates.

In some embodiments, the surface of the poppet valve is substantially parallel to the proximal reactor surface. Other suitable valves for the present techniques are known to those of skill in the art and can include rotary valves sleeve valves, slide valves, plunger valves and butterfly valves. The valves are made of a suitable material that can withstand the conditions such as temperature, steam and/or reactant exposure, pressures, reactor maintenance schedules, etc. encountered for a specific valve location within the reactor. For extreme high temperature conditions ceramics can be used, while metallic valves are suitable for most applications below this temperature. Depending on the reactor design, the poppet valve opens toward the reactor bed or opens away from the reactor bed. Certain embodiments where the poppet valve opens toward the reactor bed may be preferred because of ease of managing flow and pressure drop in the piping and/or head design. Certain embodiments where the poppet valve opens away from the reactor bed may be preferred for two reasons. First, to relieve pressure in an over pressurized reactor, e.g., where the pressure is sufficient to overcome the force generated by a biasing closure spring. This can obviate the need for separate pressure relief valves and can be useful where a reactor is susceptible to rapid pressure buildup. Moreover, such embodiments provide less dead space in the reactor than those where poppet valve opens towards the reactor bed. A flow distributor is useful in such embodiments to control resulting different flow patterns and fills up additional dead space in the reactor.

In certain other embodiments, a gas distributor mechanism may be positioned between the valves and bed surface. An example gas distributor mechanism is described in U.S. Patent Application Publication No. 2007/0144940. The gas distributor mechanism may function to direct gas to select channels within the bed. In a preferred embodiment, the spacing between the fully-open valves and the bed surface, such as between 5 to 200% of the disk element diameter, provide sufficient space for such distributors. However, the presence of such mechanisms, as well as other reactor features, such as bed support structures, may result in a modified spacing and/or result in the selection of bed-valve spacing at the higher end of the preferred range.

Typically, the distance during operation between the poppet valve disk element flat or profiled surface in the fully open position and the reactor bed surface is between 5% and 200% of the disk element diameter, preferably, between 20% and 80% of the disk element diameter. The poppet valve typically comprises a poppet valve stem element, or rod, extending to a location outside its head. The valve stem can be surrounded by a bushing and/or valve guide which provides support of the valve while allowing movement along a linear path to guide and, in some cases, seals the valve during operation. In some embodiments, a valve stem seal is associated with the valve stem, e.g., rod packing as is typically seen in reciprocating compressors. For present purposes, in some instances a valve stem seal can be the same as a bushing or valve guide, although a separate valve seal is less susceptible to wear in use.

In certain embodiments of the reactor, each valve is associated with an externally accessible valve seat that fits within its respective inlet to the reactor body and/or outlet from the reactor body and is sealed to the head by any suitable sealing means, e.g., a gasket which is held in place by the flange attaching the valve assembly to its respective inlet. Alternatively, the valve assembly can be attached to its respective inlet via a rotatable locking mechanism, e.g. a turn-to-lock or bayonet mechanism. In other embodiments, the valve seat can be installed in the head separate from the valve assembly by use of threaded-in or pressed-in seats, or by the machining of the valve seat into the head itself.

In some embodiments, the poppet valve comprises a linearly actuatable valve stem engageable with an actuator to open and close the valve by imparting linear motion thereto. The actuator is at least one of pneumatically actuated, hydraulically actuated, and electromagnetically actuated, in at least one direction. In other embodiments the actuator can be actuated by a camshaft, in at least one direction. An alternate return mechanism can be used, e.g., a spring, in certain embodiments, e.g., with a valve closing bias. An alternate actuation approach employs a common actuator on linearly aligned plural valves common to a particular fluid flow stream.

Poppet valves in certain embodiments can comprise a circular disk element connected to a solid cylindrical stem element. Diameter of the poppet ($D_P$) (subscript "P" for poppet valve) can be measured across the disk element. Lift, ($L_P$) can be measured as the distance that the poppet valve is translated to create open area for flow. An assembly of poppet valves can also be characterized in terms of the spacing between the valves. The spacing ($S_P$) describes the center to center spacing. Thus, if two equal diameter ($D_P$) valves have a spacing that is exactly equal to $D_P$ (i.e. 100% of $D_P$), the two poppet disk elements may just touch each other on their circumference. Valve spacing, or spacing between valves, can be characterized as the center-to-center measurement of the valves as a percent of the valve diameter ($D_P$). As the valves get closer together they tend to create a flow restriction on the inside of the reactor, as well as a constructability issue on the outside. Moreover, large valve spacings create concerns about flow area sufficiency and flow distribution into the bed. Accordingly, suitable valve spacing should balance these opposing factors. Spacing of the valves is typically between 120% and 400% of the valve diameter, preferably, between 140% and 200%. For spacing between valves of different diameter, the average diameter may be used as divisor. This preferred spacing applies to each of the adjacent valves on a given head, regardless of whether those valves carry the same stream. It is not expected that each of the adjacent valves has identical spacing, but it is preferred that each of the adjacent valves have is spacing within the ranges provided.

In certain embodiments, the circular poppet valves associated with a particular head are substantially circular, uniform in diameter and spaced center-to-center by 120% to 400% of the average poppet valve disk element diameter, preferably, spaced center-to-center by 140% to 200% of the average poppet valve disk element diameter.

In some embodiments, the reactor provides at least one of: i) a valve pressure drop as fluid flows through a valve of from 1% to 100% of the reactor internal pressure drop; ii) a ratio of total stream poppet valve flow area for one of an inlet stream and an outlet stream to reactor flow area ranging from 1% to 30%; iii) a poppet valve diameter between minimum value $D_{PMIN}$, which is defined in the equation 1 (e1) below:

$$(D_{PMIN}) \text{ [inches]}=0.1484+0.4876*D_B \text{ [feet]}, \quad \text{e1}$$

$$(D_{PMIN}) \text{ [cm]}=0.3769+0.0406*D_B \text{ [cm]} \quad \text{e1a}$$

where $D_B$ is flow area diameter in the units indicated in the square brackets, and a maximum value ($D_{PMAX}$), which is defined in the equation 2 (e2) below:

$$(D_{PMAX}) \text{ [inches]}=1.6113+1.8657*D_B \text{ [feet]}, \quad \text{e2}$$

$$(D_{PMAX}) \text{ [cm]}=4.0927+0.1555*D_B \text{ [cm]} \quad \text{e2a}$$

where $D_B$ is flow area diameter in the units indicated in the square brackets; iv) $L_P/D_P$, (the ratio of valve lift to poppet diameter) ranges between 3% and 25%; and v) valve lift times of at least 50 milliseconds. As may be appreciated, the poppet flow area $A_{PFI}$ relates to the diameter, the lift and the number of valves, and is defined by the equation 3 (e3) below:

$$A_{PFI}=N_{FI}*\pi*D_{PFI}*L_{PFI}, \quad \text{e3}$$

where FI is "forward flow inlet," A is area, N is number of valves, D is diameter, and L is lift.

Typically, the reactor provides at least one of: i) a valve pressure drop as fluid flows through a valve of from 5% to 20% of the reactor internal pressure drop; ii) a ratio of total stream poppet valve flow area for one of an inlet stream and an outlet stream to reactor flow area ranging from 2% to 20%; iii) a poppet valve diameter between minimum value ($D_{PMIN}$) [inches]=0.1484+0.4876*$D_B$ [feet], where $D_B$ is flow area diameter in feet, and maximum value ($D_{PMAX}$) [inches]= 1.6113+1.8657*$D_B$ [feet], where $D_B$ is flow area diameter in feet; iv) $L_P/D_P$, (the ratio of valve lift to poppet diameter) ranges between 5% and 20%; and v) valve lift times between 100 and 500 milliseconds. Further, the ratio of total stream poppet valve flow area for a particular inlet stream or outlet stream to reactor flow area is between 1% to 30%, preferably, between 2% and 20%.

Figure 3:
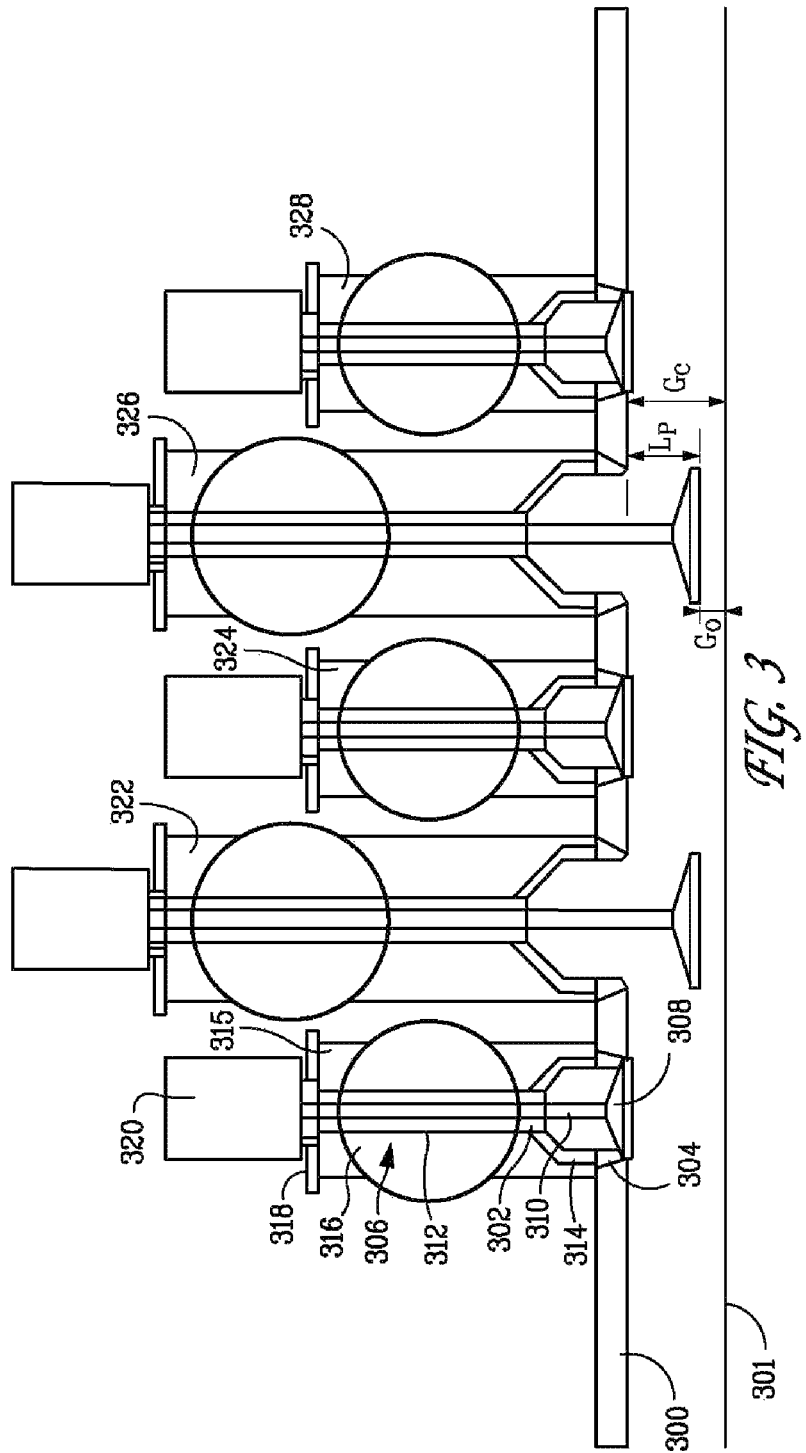
FIG. 3 is an illustration valve assemblies and manifolds as associated with a flat reactor head for use in the reactor according to an embodiment of the present invention.

The reactor in certain embodiments can also be characterized in terms of the is distance, or gap, that is created between the poppet and the bed packing. For instance, open gap ($G_O$) is the distance between the reactor bed surface and the flat or profiled surface of the poppet that is facing the proximal reactor bed surface when the valve is open, and define the closed gap ($G_C$) as the distance when the valve is closed. In many embodiments (such as illustrated in FIG. 3) the difference between these values ($G_C$-$C_O$) is equal to lift, $L_P$.

The use of poppet valves enables high flow rates by means of the large flow areas that are provided when the valves are opened. Flow area is generally known as the product of the valve circumference ($\pi*D_P$) and valve lift ($L_P$). In poppet valves, as in other valves, there is some reduction of pressure (called pressure drop) that occurs as fluid flows through the valve. Similarly, there is a pressure drop that occurs as fluid flows through the flow path comprising the reactor internal contents between the valves. A suitable range for the ratio of valve pressure drop to total reactor pressure drop enables the balancing of opposing factors, with low valve pressure drop preferred for flow distribution within the bed, and high valve pressure drop preferred for high flow rates and smaller/fewer valves. Thus, valve pressure drop is typically between 1% and 100% of the reactor internal pressure drop, preferably, between 5% and 20% of reactor internal pressure drop.

Many applications of the poppet valve reverse flow reactors are advantageously specified in terms of the poppet valve flow area for each stream as percent of the reactor flow area, with each stream's poppet valve flow area being calculated from the number and character of the poppet valves on that stream, and with reactor flow area calculated as the cross-sectional area of the reactor bed that is accepting or discharging the flow. For example, considering a set of $N_{FI}$ poppet valves (where FI=forward inlet) that are serving the stream that is the flow inlet for the forward flow direction, the total poppet valve flow ($A_{PFI}$) area is $N_{FI}*\pi*D_{PFI}*L_{PFI}$. For a typical cylindrical reactor, with flow along the cylinder's axis, $D_B$ is the bed diameter, and consequently $\frac{1}{4}\pi D_B^2$ is the reactor flow area. A typical suitable range for the ratio of total stream poppet valve flow area to reactor flow area balances opposing factors as does pressure drop. The number and size of valves for each particular inlet or outlet stream can be chosen to provide a ratio of poppet valve flow area for a particular inlet or outlet stream to reactor flow area between 1% to 30%, preferably, between 2% and 20%. In other words, flow through the poppet valve flow area for forward flow inlet or reverse flow outlet can be between 1% to 30%, preferably, between 2% and 20%, as a percentage of reactor flow area. Many applications of the reverse flow reactor in some of the embodiments are advantageously specified in terms of the specific poppet valve diameter and lift. Poppet valve diameter ($D_P$) is advantageously specified in proportion to the diameter ($D_B$) of the reactor flow area. For non-cylindrical reactor flow area, an equivalent diameter may be computed as $(4A/\pi)^{1/2}$. A suitable range of diameters satisfactorily balances the opposing needs for high flow rates, uniform flow distribution, and minimal complexity. Preferred poppet diameter is not a simple fraction of diameter, but typically varies continuously as bed diameter changes. The range of poppet valve diameters can be between a minimum value ($D_{PMIN}$) and a maximum value ($D_{PMAX}$), wherein these minimum and maximum values are expressed as a function of bed diameter in the following equations: $D_{PMIN}$ [in]=0.1484+0.4876*$D_B$ [ft] and $D_{PMAX}$ [in]=1.6113+1.8657*$D_B$ [ft].

A suitable range for the ratio of valve lift ($L_P$) to poppet diameter ($D_P$) balances the factors of valve pressure drop, valve efficiency, bed flow uniformity, and improved mechanical complexity. Valve lift ratio ($L_P/D_P$) is typically between 3% and 25%, preferably, between 5% and 20%.

Further to the above-described dimensions for poppet flow area, diameter, and lift, poppet flow area can be related to diameter, lift, and number of valves by the following geometric equation: $A_{PFI}=N_{FI}*\pi*D_{PFI}*L_{PFI}$ (example for one stream; FI subscript represents forward inlet). The number of valves suitable in a reactor is the result of reactor design according to specifications made for other parameters. Design according to the specification provided herein results in valve numbers that balance several opposing objectives. Use of fewer valves leads to those valves being larger to satisfy flow area requirements. Larger valves require larger lifts and larger valve-bed gaps ($G_O$), thus increasing the distance between the reactor head and the reactor bed resulting in more open flow path volume. Too many valves in themselves add to reactor costs in addition to requiring more intricate manifolds. Exemplary designs incorporating these features can be found in Examples 1 and 2, as well as FIGS. 1 and 2.

Reactors in one or more embodiments of the present invention allow for an unexpectedly small gap in between the valve assembly and the entry into the reactor bed. Minimizing this gap advantageously minimizes reactor open flow path volume which is deleterious to reverse-flow reactor efficiency. Open flow path volume is associated with the space between the reactor beds and the valves. Open flow path volume is lacking of any substantial amount of catalyst, packing, or heat transfer solids, and thus provides essentially no contribution to the gas stream treating that occurs within the reactor. However, fluids within the open flow path volume are still within the flow path and thus may be transferred is from one step to the next when the flow direction is reversed or else may require purging fluid to be recovered before the flow direction is reversed. One or more embodiments of the present invention reduce open flow path volume resulting in lower purging requirements and/or lower product losses from one step to the next. Critical heat transfer properties of the packing used are well known in the pressure swing reforming art and result in unexpected flow distribution properties when poppet valves are used and positioned as specified in the present invention. Distribution space, characterized as the height between the open poppet valve and the reactor bed surface, may be minimized in the reactor. The bed-to-poppet height ($G_O$) for inlet valves is typically from 20% to 80% of the diameter of the poppet. Because good flow distribution is less of a concern for outlet or exhaust valves, the minimum bed-to-poppet height can be less than for the inlet or intake valves. Typically, the bed-to-poppet height ($G_O$) for outlet valves ranges from 5% to 80% of poppet diameter. These values represent attractive minimum gap dimensions. Larger gaps may be used to accommodate other reactor internals, such as bed supports or fuel distribution systems.

Valve lift times in a representative example of an industrial diesel engine are approximately 0.004 seconds (4 milliseconds). Typically these valves are opened utilizing a cam shaft, and the valve opens over a certain crank angle, typically going from fully closed to fully open in approximately 25 degrees of crankshaft rotation. The valves that are used in the reactor may open utilizing a pneumatic actuator and can be held in the fully open position for a length of time before closing. The opening and closing time for the valves is based on the total cycle time for the reactor. Poppet valves as used in some of the embodiments of the present invention have lift times that are unanticipated in the poppet valve engine art. Valve opening timing is distinguished because the rate of valve opening controls velocity changes within a reverse-flow bed system, and these changes impact the bed performance and durability. Valve lift times that are too fast, such as those used in engines, are undesirable in the present techniques because such times result in too-rapid changes in bed velocity. Typically, the lift times of the valves may be greater than 50 milliseconds, e.g., between 50 and 1000 milliseconds, preferably between 100 and 500 milliseconds. The duration of a complete cycle is defined as $\tau$, and the total lift of the valve is defined as $\lambda$. Typically, a process employing reactors uses a set of two or more reactors such that one or more reactors are operating in the forward direction while one or more other reactors are operating in the reverse direction. A single reactor may remain in a forward or reverse flow step for a duration of about 15% to about 80% of the total cycle time ($\tau$), depending on the number of reactors and design of the cycle. The lift times of the valves can range from $0.01\tau$ and $0.05\tau$.

As earlier noted, in a second aspect the present invention relates to a reactor comprising: a) a reactor body partially enclosing a reaction and/or heat exchange region comprising two substantially opposing open ends; b) a first head capping one end of the reactor body; c) a second head capping the opposing end of the reactor body; d) a fixed bed comprising a region proximal to the first head, a region proximal to the second head and a central region disposed therebetween, which fixed bed is disposed within the reactor body and comprises solid material capable of promoting heat exchange and/or reaction of a gas stream; e) at least one gas stream inlet associated with the first head opening a pathway through the first head and into the reactor body and at least one gas stream outlet associated with the second head opening a pathway from the reactor body and through the second head; f) at least one inlet poppet valve controlling the gas stream inlet and integrated with the head associated with the inlet, the inlet poppet valve comprising a linearly actuatable valve stem; g) at least one outlet poppet valve controlling the gas stream outlet and integrated with the head associated with the outlet, the outlet poppet valve comprising a linearly actuatable valve stem; and h) at least one actuator engageable with the linearly actuatable valve stem of f) and/or g) providing valve opening and closing by imparting linear motion to the poppet valve to allow gases to pass from outside the reactor to inside the reactor body, and from inside the reactor body to outside the reactor so as to provide changeable flow operation.

In certain embodiments of this aspect, the reactor further comprises i) at least one gas stream inlet associated with the second head opening a pathway through the second head and the reactor body and at least one gas stream outlet associated with the first head opening a pathway through the reactor body and the first head, with associated inlet poppet valve(s) or other inlet flow control means, outlet poppet valve(s) and actuator(s) analogous to f), g) and h).

A third aspect, earlier noted, relates to a process for rapid stream-switching of at least two streams in a reverse-flow reactor comprising a reactor body partially enclosing a reaction and/or heat exchange region comprising two substantially opposing open ends with a first head capping one end of the reactor body, a second head capping the opposing end of the reactor body, a fixed bed disposed within the reactor body comprising solid material capable of promoting heat exchange and/or reaction of a gas stream. The process comprises: i) introducing from one or more inlet gas sources at least one first gas stream to at least one gas stream inlet associated with the first head through the first head and into the reactor body and withdrawing a treated first gas stream from the reactor body and through the second head to at least one gas stream outlet associated with the second head; wherein said introducing and withdrawing are controlled respectively by at least one intake poppet valve located in the first head and at least one exhaust poppet valve located in the second head; and ii) introducing from one or more inlet gas sources at least one second gas stream to at least one gas stream inlet associated with the second head through the second head and into the reactor body and withdrawing a treated second gas stream from the reactor body and through the first head to at least one gas stream outlet associated with the first head, wherein said introducing and withdrawing are controlled respectively by at least one intake poppet valve or other intake flow control means located in the second head and at least one exhaust poppet valve located in the first head.

Reverse-flow reactor applications of particular interest can couple an endothermic reaction with an exothermic reaction, typically combustion. Endothermic reactions of particular interest include steam reforming, dry ($CO_2$) reforming, pyrolysis, catalytic cracking, dehydrogenation, and dehydration. Typical pyrolysis reactions include steam cracking reactions such as ethane, naphtha, or gas oil cracking, hydropyrolysis reactions such as methane or heavy feed hydropyrolysis to acetylene, and non-hydrocarbon cracking reactions such as $H_2S$ pyrolysis to hydrogen and sulfur. Typical dehydrogenation reactions for use with the present techniques include alkane dehydrogenations such as propane dehydrogenation and alkyl-aromatic dehydrogenations such as ethyl benzene dehydrogenation. Typical dehydration reactions for use with the present techniques include methanol and ethanol dehydration. In these applications, the reactor contains an environment that is very severe such that the durability of materials employed within the reactors is a concern. The reforming and pyrolysis environments, in particular, include high temperatures, typically ranging from 500° C. to 2000° C., e.g., from 800° C. to 1800° C., steam at partial pressures ranging from 0 to 5000 kilo-Pascals (kPa), preferably from 0 to 3000 kPa, thermal cycling at a rate of from 0.1 to 20 cycles per minute, preferably 1 to 15 cycles per minute, oxidation-reduction cycling, e.g., from streams dominated by the presence of free oxygen to streams dominated by the presence of free hydrocarbon and hydrogen, and pressure swings at total pressures ranging from 0 to 5000 kPa. The reactor of the present invention is able to reliably perform in these environments.

Examples are presented herein that apply the present techniques to both pressure swing reforming and pyrolysis applications.

An exemplary embodiment is shown in FIG. 1 below. FIG. 1 is an illustration of an asymmetric reverse flow reactor with a single head and associated valve assembly according to an embodiment of the present invention. The reactor 101 comprises a reactor body 102 with a reactor bed 103 having a substantially gas impermeable partition 104 dividing the reactor bed into left side reactor bed 105 and right side reactor bed 106. The upper portion of the reactor bed is capped by a single head 107 up to which the partition 104 extends. Inlet opening 108 in the head 107 is positioned above the left side reactor bed 105 and fed by a first conduit 109. A conduit, such as conduit 109 and 115 may be a tube or other fluid conveying means provided as a portion of or extension from a manifold (not shown). A conduit, such as conduit 109 and 115 may extend from outside head 107 to at least partially through said head. The first conduit 109 may extend from outside the reactor body 102 and through an opening in the head 107 towards the left side reactor bed 105. A forward flow inlet poppet valve 110 is seatable within the head contacting a separate valve seat inserted within the head (not shown) or the head itself when seated, and controls fluid flow from outside the head into the left upper open space 111 above the left side reactor bed 105. The inlet poppet valve 110 is upwardly extended in the closed retracted position and is open when downwardly extended. When the inlet poppet valve 110 is open, fluid flows forward from the first conduit 109 through the inlet poppet valve 110 into a flow path via the open space 111 through the left side reactor bed 105 into a lower common open space 112 below the reactor bed 103 and then to the right side reactor bed 106 and right upper open space 113 from which the flow path extends to forward flow outlet poppet valve 114 is seatable within the head 107 and contacts a separate valve seat (not shown) or the head itself when seated. The outlet poppet valve 114 which is seated within the head 107 controls flow from the right upper open space 113 to a second conduit 115 extending from the outlet poppet valve 114 through the head to a location outside the head. Like the inlet poppet valve 110, the outlet poppet valve 114 is upwardly extended in the closed retracted position and is open when downwardly extended. (An alternate arrangement can be made wherein the inlet poppet valve 110 and outlet poppet valve 114 are downwardly extended in the closed position and extend upwardly away from the reactor bed in the open position.) The second conduit 115 can be a tube or other fluid conveying means provided as a portion of or extension from a manifold (not shown)). The second conduit 115 may extend from outside the reactor body 102 and through an opening in the head 107 towards the right side reactor bed 106 and may be used to conduct reaction products from the reactor bed 103 to a location outside the reactor 101.

During operation, the inlet poppet valve 110 and outlet poppet valve 114 are substantially in phase, i.e., they open and close together substantially at the same time. Thus, when open they allow for fluid flow from the first conduit 109 to the second conduit 115. A corresponding set of valves and conduits (not shown) can provide a reverse flow along the flow path through the reactor bed in the reverse direction, with a reverse flow inlet valve over the right side reactor bed 106 and a reverse flow outlet valve over the left side reactor bed 105. The second set of valves also typically operates substantially in phase with regard to each other, while operating in substantially opposite phase with the first set of valves. Thus, the first and second valves (the first valve pair) are simultaneously open while the third inlet poppet valve and fourth outlet poppet valve (the second valve pair) are closed when flow is in the forward direction (from the left side of the reactor to the right). The first and second valves of the first valve pair are then closed while the second valve pair is open to permit flow in the reverse direction.

In an alternative embodiment, the advantages of employing a particularly symmetric valve pattern may dictate a valve diameter that is larger than the $D_{PMAX}$ that would be chosen without considering symmetry. For example, one may use a hexagon pattern of six or seven valves associated with the circular end of a cylindrical reactor bed design. If center to center valve spacing is ≥120% of valve diameter, then valves could be as large as 27.8% of reactor diameter. Further, when center to center valve spacing is ≥140% of valve diameter, then valves could be as large as 23.8% of reactor diameter. As an example, a reactor bed that is 96 inches (2.44 meters) in diameter may benefit from a valve that is 22.85 or 26.7 inches (58 or 67.8 cm) in diameter. For such embodiments, the $D_{PMAX}$ may be a larger proportion of bed diameter, as given by the equation $(D_{PMAX})$ [inches]=1.6113+2.858*DB [feet] or $(D_{PMAX})$ [cm]=4.0927+0.238*DB [cm]. As may be appreciated, other variations may also be envisioned within the scope of the present techniques.

Asymmetric reverse flow operation typically requires that the composition of gas flowing in the forward direction differ from the composition of gas flowing in the reverse direction. For example, the gas flowing through the intake valve in the forward direction differs from the composition of gas flowing through the intake valve in the reverse direction. Examples of reactions where such reactors with a single head can be employed include regenerative thermal oxidizers, which are further discussed in U.S. Patent Application Publication Nos. 2007/0144940 and 2008/0142409, the contents of which are incorporated herein by reference in their entirety.

Figure 2:
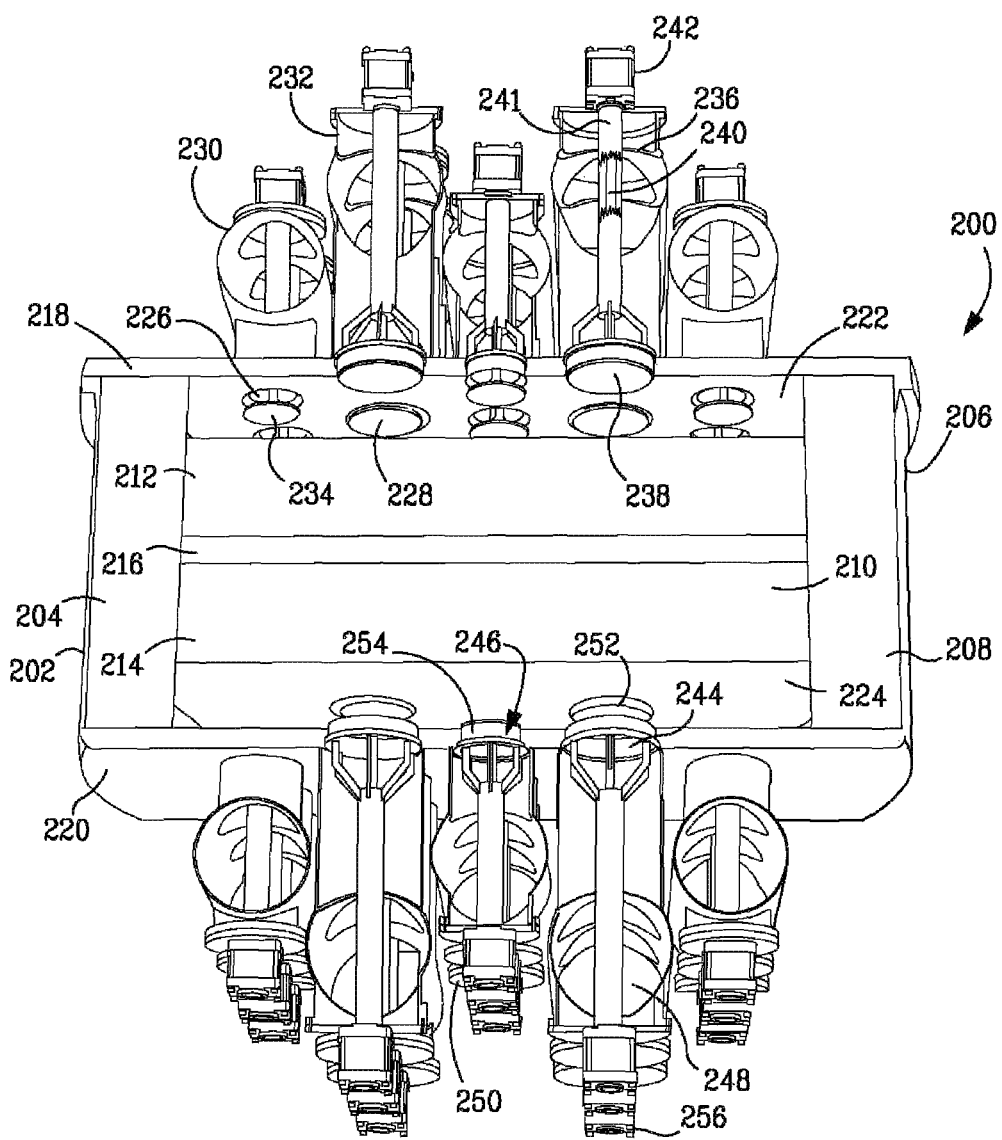
FIG. 2 is an illustration of an asymmetric reverse flow reactor with opposing flat heads and associated valve assemblies and manifolds according to an embodiment of the present invention.

An exemplary embodiment of the present reactor, as applied to a large-scale pyrolysis reactor having multiple valves and conduits, is shown in FIG. 2 below. FIG. 2 is an illustration of an asymmetric reverse flow reactor with two opposed heads and associated valve assemblies according to an embodiment of the present invention. The reactor 200 comprises a cylindrical wall and cylindrical insulation layer depicted in the cross-sectioned FIG. as left side wall 202, left insulation layer 204, right side wall 206, and right insulation layer 208. A reactor bed 210 comprises an upper reactor bed portion 212, a lower reactor bed portion 214 with a mixing zone 216 which can contain a mixing structure. The reactor is capped with an upper head 218 and a lower head 220, resulting in an upper open zone 222, and lower open zone 224 which open zones are comprised substantially of open flow path volume. Such open flow path volume in reverse flow reactors contains gas that may cross over from the forward flow step of the cycle to the reverse flow step, and vice versa, if not properly managed, for example by flushing between these steps of the cycle. This minimizing of open flow path volume advantageously reduces the volumes which to be managed during a cycle, reducing cycle time and increasing efficiency. The upper head 218 and lower head 220 contain openings in which valve structures can be inserted. The upper or lower open flow path volume between the head and reactor bed can also contain distribution lines (not shown) which directly introduce fuel for combustion in the reactor 200.

The upper head 218 contains various openings, such as exemplary openings 226 and 228 (the latter opening depicted as occupied by a poppet valve) for forward flow inlet manifold 230 and reverse flow outlet manifold 232. Disposed through the manifolds and controlling the openings are forward flow inlet valve 234 and reverse flow outlet valve 236. The forward flow inlet valve 234 and reverse flow outlet valve 236 are poppet valves comprising (as depicted in the case of 236) a disk element 238 connected to a stem element 240 which can be positioned within a bushing or valve guide 241. The stem element 240 is connected to an actuating means 242 which imparts linear motion to the valve. As may be appreciated, the openings 226 and 228 and associated manifolds 230 and 232 may form conduits extending from outside the upper head 218 to at least partially through the upper head 218 for fluid flow. This exemplary embodiment advantageously has an independent actuating means associated with each valve which minimizes actuating means failure to a single valve. Alternately, a single actuating means can be provided that controls plural valves. In general, the openings and inlet valves for inlet manifolds are of smaller diameter than those for outlet manifolds, given that the reactant volumes passing through the inlets tend to be lower than product volumes passing through the outlets. In FIG. 2, the forward inlet valves are depicted in an open position while the reverse outlet valves are depicted in the closed position.

A similar manifold and valve arrangement is associated with the lower head 220. The lower head 220 contains various openings, such as exemplary openings 244 and 246 for forward flow outlet manifold 248 and reverse flow inlet manifold 250. (Opening 246 is partially obscured inasmuch as the reverse flow inlet valve 254 is depicted in the closed position.) The "tag" to 246 is an arrow, pointing through the reverse flow inlet valve 254 and into the opening 246. The openings 244 and 246 and associated manifolds 248 and 250 may form conduits extending from outside the lower head 220 to at least partially through said lower head 220 for fluid flow. Disposed through the manifolds and controlling the openings are forward flow outlet valve 252 and reverse flow inlet valve 254. Again, the forward flow outlet valve 252 and reverse flow inlet valve 254 are poppet valves comprising a disk element connected to a stem element which can be positioned within a bushing or valve guide. As shown for forward flow outlet valve 252, the stem element is connected to an actuating means 256 which imparts linear motion to the valve, similar to the discussion above. The embodiment advantageously has an independent actuating means associated with each valve which minimizes actuating means failure to a single valve. Alternately, a single actuating means can be provided that controls plural valves operating in phase, preferably, a group of plural reverse flow inlet valves. Part of the reactor valve design includes sealing the reactor, specifically around the valves, to eliminate release of reactant and product gases. Suitable seals include rod packing, e.g., reciprocating compressor type seals for the stem elements or shafts of the valves. Valve actuator means provides adequate force and lift times, and meets the design life of the reactor. Typically, the actuator means are pneumatically controlled actuators that are spring returned and are biased to closure in the event of actuator failure.

In FIG. 2, the reverse flow outlet valves (236) are depicted in the closed position while the forward flow inlet valves (234) are depicted in an open position. Thus, FIG. 2 depicts reactants in forward flow from the forward flow inlet manifold 230 of the upper head 218, through the reactor bed 210 and into the forward flow outlet 244 of the lower head 220. Both reverse flow valves (reverse flow outlet valve 236 and reverse flow inlet valve 254 are closed at this time. In the next phase of the cycle the forward flow inlet valves (234 and 252) close and the reverse flow inlet valve 254 of the lower head opens along with the reverse is flow outlet valve 236 of the upper head 218, promoting reverse flow of gas from the lower head 220 through the reactor bed 210 and out the upper head 218.

Typically, the forward flow valve pairs, with each valve pair consisting of a forward flow inlet valve and forward flow outlet valve operate together in phase with each member of the pair. A forward flow valve pair can be located on their respective heads directly opposite each other with stems parallel to the reactor sides and driven by a common actuator means. Similarly, the reverse flow valve pairs, with each valve pair consisting of a reverse flow inlet valve and a reverse flow outlet valve operate in phase with each other and can, if desired, be located in their respective heads directly opposite each other with their stems parallel to the reactor sides and driven by a common actuator means. Generally, forward flow valve pairs operate directly opposite with reverse flow pairs, such that when a forward flow valve pair is open, the reverse flow valve pair is closed, and vice versa. Where each valve on the reactor has its own actuator means, the reactor can continue to operate if only a single valve fails and allows the removal and replacement of a single valve without the need to disassemble the entire reactor. Alternately, plural valves that control the same feed/product stream can be driven by a common actuator.

The reactor bed 210 comprises an upper reactor bed portion 212, a lower reactor bed portion 214 with a mixing zone 216 which can contain a mixing structure. The lower reactor bed may also include structures that support the weight of the bed (not shown). Typical reactor bed materials include honeycomb monoliths, which have straight channels to minimize pressure drop and enable greater reactor length. Honeycomb monoliths used in the reactor typically have channel densities that range from about 16 channels per inch (channels/in$^2$) to about 3200 channels/in$^2$ (2.5-500 channels/cm$^2$). Alternatively, packing for one or more portions of beds 212 and 214 may be more tortuous, such as foam monoliths and packed beds. Typical foam monoliths for the present techniques have pore densities that range from about 5 ppi (pores per inch) to about 100 ppi (i.e. 2-40 pore/cm). Typical packed beds for the present techniques have packing with wetted surface area that range from about 60 per feet (ft$^{-1}$) to about 3000 ft$^{-1}$ (i.e. 2-100 cm$^{-1}$). The total flow path in FIG. 2 is represented by the volumes in open zones 222 and 224 as well as volumes in beds 212 and 214 and in mixer 216. Open flow path volume is comprised mostly of the open zones 222 and 224, while packed flow path volume is comprised mostly of the bed and mixer zones 212, 214, and 216.

The integration of large poppet valves into the heads of the reactor greatly reduces, relative to conventional valving, the amount of unproductive volume between the reactor bed and the valve. Moreover, this embodiment is readily constructed and operated, with a sufficient number of valves arranged on a reactor head to provide sufficient flow area to allow operation at desired pressure drop, typically a valve pressure drop between 1% and 100% of the reactor internal pressure drop, preferably, between 5% and 20% of reactor internal pressure drop. Reactor internal pressure drop, in the context of FIG. 2, may comprise the difference in pressure between the upper open zone (222) and the lower open zone (224). Valve pressure drop, in the context of FIG. 2, comprise the difference in pressure between a manifold (e.g. 230) and the open zone (e.g. 222) just beyond an open valve (e.g. 234). As stated earlier, valve pressure drop is typically between 1% and 100% of the reactor internal pressure drop, preferably, between 5% and 20% of reactor internal pressure drop. Moreover, flow emerging from the valves can be adequately distributed over the entire width of the bed. This embodiment can be used with a reactor bed substantially comprising parallel channels in the direction of flow as noted in the preceding paragraph, e.g., honeycomb monoliths which can eliminate any radial dispersion of streams. Advantaged reverse-flow reactor technology provides high velocity uniformity across the bed cross-section, for example as quantified via the standard deviation of velocity so that residence times in axial paths through the bed may be similar. In particular, reverse flow reactor technology used for pressure swing reforming and pyrolysis requires a high degree of flow distribution in the open volume outside of the reactor bed packing, because the parallel channel components, e.g., those in honeycomb structures, limit further redistribution of flow once inside the bed. The present techniques are particularly useful in providing a head-integrated poppet valve reactor that distributes flow from integrated poppet valves into a parallel channel honeycomb bed packing.

FIG. 3 illustrates a detailed vertical cross-section of the reactor upper head 300 showing associated integral valve assemblies in place within the manifolds, above a reactor bed surface 301. Forward flow inlet valve assembly 302 comprises valve seating means 304 which interfaces between the head and valve assembly and is attached into an opening in the head to provide a forward inlet opening in the head. The forward flow inlet valve assembly 302 further comprises a poppet valve 306 having a disk element 308 connected to a stem element 310 which is surrounded in part by a hollow cylindrical valve guide member 312 from which extend support arms 314 which connect the valve seating means to the valve guide means. The forward flow inlet valve assembly 302 extends through a vertical manifold tube 315 acting as a delivery tube to the valve opening. The vertical manifold tube 315 intersects with a horizontal manifold tube 316 through which inlet reactant gas is conducted to the valve and therethrough ultimately introduced to the reactor bed 301. Fluid flows from the horizontal manifold tube 316 and vertical manifold tube 315 at least partially through the opening in the head 300 which provides a conduit for fluid flow from outside head 300 to at least partially through said head, with flow continuing past the valve seating means 304 when the poppet valve 306 is in an open position. The conduit may include the valve seating means 304, hollow cylindrical valve guide member 312, vertical manifold tube 315, horizontal manifold tube 316, valve actuating member 320 and/or assembly's collar 318 for inlet valve assembly 302. The vertical manifold tube 315 is capped by the valve assembly's collar 318 through which extends the valve guide member 312 and valve stem member 310. Atop the collar 318 is a valve actuating member 320 which pneumatically controls the linear movement of the valve stem element and thus the passage of fluid through the forward flow inlet opening that is surrounded by the valve seating means 304. A larger diameter reverse flow outlet valve assembly 322 is attached at a reverse flow outlet opening in the upper head. Valve assemblies 324, 326, and 328 represent additional valve assemblies, namely, a forward flow inlet valve assembly 324, a reverse flow outlet valve assembly 326, and another forward flow inlet valve assembly 328, respectively. Each additional valve assembly is analogous to the forward inlet valve assembly described above. Forward flow inlet valve assemblies 320, 324, and 328 are shown with their valves in the closed position while reverse flow outlet valve assemblies 322 and 326 are shown with the valve in the open position, showing $L_P$, or lift, $G_O$, or open gap, and $G_C$, or closed gap.

Each valve assembly comprises, a valve seat, a disk that mates up with the valve seat, a stem that is attached to the disk, a guide for the stem, an attachment structure from the valve seat to the guide, linear bearings, seal systems, and an actuator. The valve seat may be attached to the guide and assembled prior to installing into the head, may be pressed or threaded into the head, or may be machined into the head, as in the case where an integral head that included the manifold and valves may be utilized. The disk may be circular, elliptical, hemispherical, or any desired shape that allows for the attachment of a stem to actuate the disk. The circular or elliptical disk may be the most efficient shape. The guide for the valve stem includes the linear bearings and the seals for the valve stem. The actuator may be an electromagnetic actuator, pneumatic actuator, hydraulic actuator, or a cam shaft that rotates at the rate desired for the process which is dependent on cycle times. The actuator may impart motion to several valves simultaneously or may impart motion to each valve individually. In the case where the valve seat is attached to the guide, the valve assembly, which may include the components listed above, can be readily removed from the reactor head as a unit facilitating the repair of the reactor should valve assembly replacement be necessary. The assembly can be attached into the reactor head by a bolt on flange at the top of the manifold. Alternatively, a turn-to-lock type (or bayonet) system where the valve assembly is inserted and the valve assembly is turned until it locks into place. This, however, is less preferred for larger valves and higher temperature streams.

In alternate embodiments, each integral valve assembly comprises, a valve seating means securable to the opening in the head, support arms securing the valve seating means to a hollow valve guide, a valve stem element within the valve guide secured to a disk member whose linear adjustment varies flow into the reactor, a collar surrounding the valve guide which collar is securable to the upper opening of a vertical manifold tube, atop which is positioned the actuating member which imparts linear movement to the valve stem element to which it can contact. Each integral valve assembly can be readily removed from the reactor head as a unit, facilitating the repair of the reactor should valve assembly replacement be necessary. Valve seat assemblies are typically attached to the head via a flange at the top of the manifold, with the integral assembly being lowered down into position through the manifold. This arrangement requires the valve assembly to be sealed in three places. The flange is sealed with a gasket, the valve stem is sealed using a reciprocating compressor seal, and the valve seat to the head of the reactor is sealed using a lip seal. An alternate means to attach and seal the valve assembly into the reactor may be a turn-to-lock type (or bayonet) system where the assembly is inserted and the entire assembly is turned until it locks into place. This, however, is less preferred for larger valves and higher temperature streams. In some embodiments of the invention, particularly where the valve opens into the manifold rather than into the reactor, or where the head is removable for installation and removal of the valve, the valve seat is installed in the head separate from the valve assembly, by use of threaded-in or pressed-in seats, or by the machining of the valve seat into the head itself. Non-integral valve assemblies like those in an automotive type engine can also be used.

Figure 4:
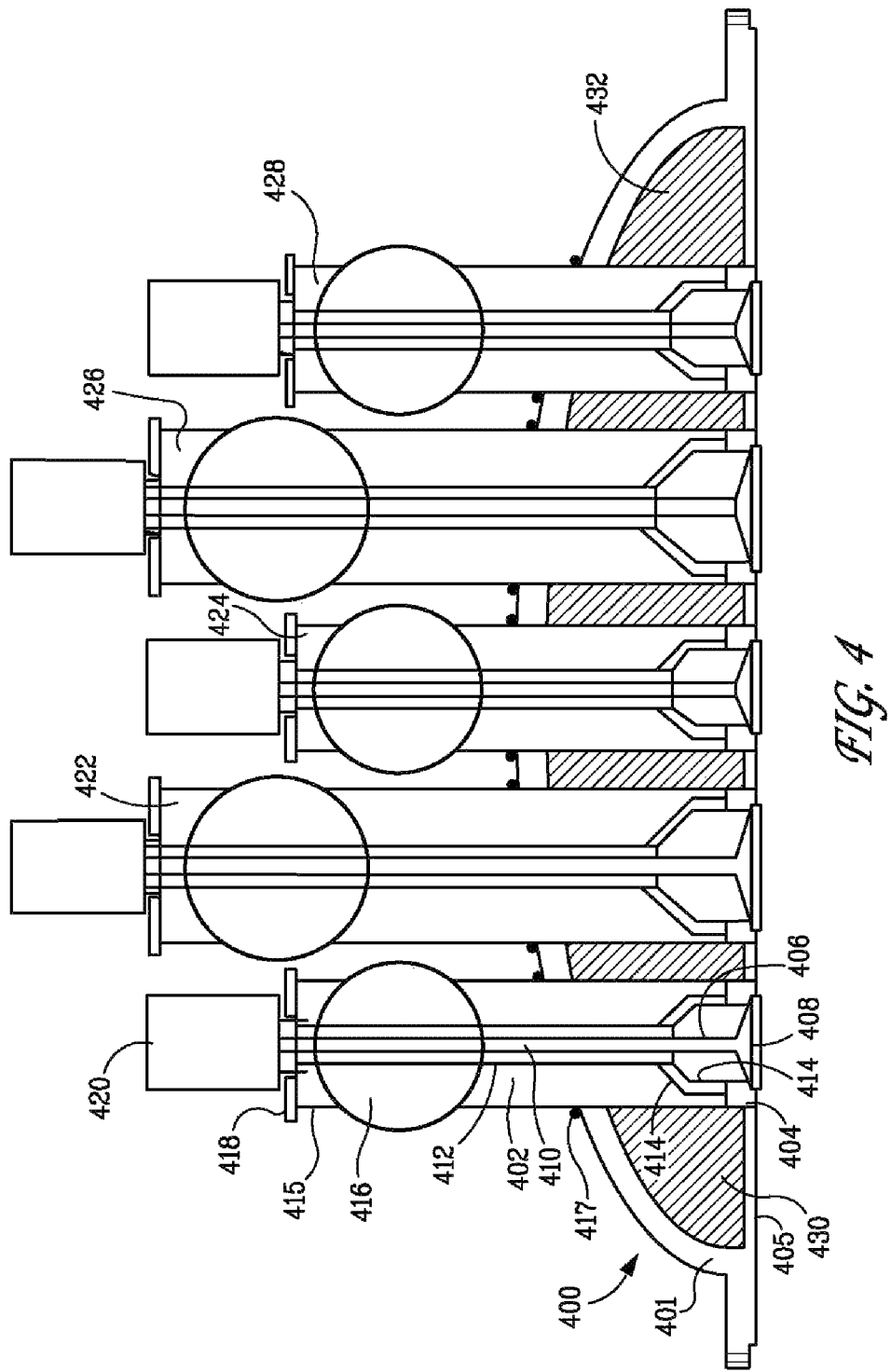
FIG. 4 is an illustration valve assemblies and manifolds incorporated in a dished elliptical head of an asymmetric reverse flow reactor according to an embodiment of the present invention.

FIG. 4 depicts a detailed vertical cross-section of a dished, substantially elliptical upper head 400 along with associated integral valve assemblies in place within an associated manifold. The exterior of the head is defined by a substantially elliptical external wall 401 which is of sufficient thickness to contain operating pressures encountered during use. Forward flow inlet valve assembly 402 comprises valve seating means 404 which is attached at a forward inlet opening in the flat floor 405 of the head which abuts the reaction zone of the reactor and provides a barrier. This flat floor 405 provides a surface on which to attach the valve seating means 404, but does not operate as a pressure boundary. The forward flow inlet valve assembly 402 further comprises a poppet valve 406 having a disk element 408 connected to a stem element 410 which is surrounded in part by a hollow cylindrical valve guide member 412 from which extend support arms 414 which connect the valve seating means to the valve guide member 412. The forward flow inlet valve assembly 402 extends through a vertical manifold tube 415 acting as a delivery tube to the valve opening in the floor 405. The vertical manifold tube 415 intersects with a horizontal manifold tube 416 through which inlet reactant gas is conducted to the valves and therethrough ultimately introduced to the reactor bed (not shown). Fluid flows from the horizontal manifold tube 416 and vertical manifold tube 415 at least partially through the opening in the flat floor 405 which provides a conduit for fluid flow past the valve seating means 404 when the poppet valve 406 is in an open position. This conduit extends from outside head 400 to at least partially through said head, and may include all or parts of the valve seating means 404, valve guide member 412, vertical manifold tube 415, horizontal manifold tube 416, valve actuating member 420 and/or assembly's collar 418 for inlet valve assembly 402. The vertical manifold tube 415 can be secured to the elliptical external wall 401 by welds 417 and is capped by the valve assembly's collar 418 through which extends the valve guide member 412 and valve stem member 410. Atop the collar 418 is a valve actuating member 420 which pneumatically controls the linear movement of the valve stem element 410 and thus the passage of fluid through the forward inlet opening that is surrounded by the valve seating means 404. A larger diameter reverse flow outlet valve assembly 422 is attached at a reverse flow outlet opening in the upper head. Valve assemblies 424, 426, and 428 represent additional valve assemblies, namely, a forward flow inlet valve assembly 424, a reverse flow outlet valve assembly 426, and another forward flow inlet valve assembly 428. Each valve assembly is similar to the forward inlet valve assembly described above in detail. The open space between the external elliptical wall 401 and the flat floor of the head 405 and between the vertical manifold tubes can be filled with a suitable space filling solid, e.g., a low porosity material with adequate temperature resistance, preferably a low porosity ceramic material, to avoid the undesired buildup of gases within the head itself, as shown at 430 and 432.

EXAMPLES

The foregoing specification is elucidated by means of examples using poppet valve reverse-flow reactor designs. The details of the designs are quantified in TABLE 1 below.

Example 1

Pressure Swing Reforming Reactor

A small pressure swing reforming reactor has a (6 cm D×24 cm L) reactor bed that executes combustion chemistry at lower pressure in the forward direction (adding heat to the bed) and steam reforming chemistry at higher pressure in the reverse direction (using the heat to convert hydrocarbons to synthesis gas). Design specifications are given in TABLE 1 for the lower reactor head containing the forward flow inlet poppet valves of the reverse flow reactor (through which forward flow reactants, e.g., air and optional diluent are introduced to the reactor bed), as well as reverse flow outlet poppet valves (from which reverse flow products, e.g., CO and $H_2$ are removed from the reactor bed). The other side of the reactor including the upper reactor head associated with the reverse flow inlet valves (through which reverse flow reactants, e.g., hydrocarbon and water are introduced to the reactor bed) and forward-outlet poppet valves (from which forward flow products, e.g., $CO_2$ and $H_2O$ are removed from the reactor bed) is designed to similar specification for the outlet valves, but employs much smaller inlet valves to meter liquid fuel into the bed system where that fuel vaporizes.

Forward flow inlet flow area ($A_{PFI}$) is 8.3% of reactor flow area. Reverse flow outlet flow area ($A_{PRO}$) is 5.6% of reactor flow area. For this reactor diameter, minimum and maximum valve sizes may be 0.62 cm (0.25 inches) ($D_{PMIN}$) and 5 cm (2.0 inches) ($D_{PMAX}$), respectively. Actual valve sizes are 3.8 cm (1.5 in) and 2.5 cm (1.0 in), for the forward-inlet and reverse-outlet valves, respectively. Valve lift is 5.8% and 8.6% of poppet diameter for the forward-inlet and reverse-outlet valves, respectively.

Example 2

Pyrolysis Reactor

The pyrolysis reactor provides a large (3.6 m D×1.2 m L) reactor bed that executes combustion chemistry at low pressure in the forward direction, adding heat to the reactor bed, and pyrolysis chemistry at low pressure in the reverse direction, using the heat to convert hydrocarbons ranging from methane to heavy oils to unsaturates, e.g., acetylene, ethylene, propylene, etc. Design specifications are given in TABLE 1 for the upper reactor head containing the forward flow inlet poppet valves of the reverse flow reactor (through which forward flow reactants, e.g., air and optional diluent, are introduced to the reactor bed), as well as reverse flow outlet poppet valves (from which reverse flow products, e.g., acetylene and hydrogen are removed from the reactor bed). The other side of the reactor including the lower reactor head associated with the reverse flow inlet poppet valves (through which reverse flow reactants, e.g., hydrocarbon and steam and/or hydrogen are introduced to the reactor bed) and forward-outlet poppet valves (from which forward flow products, e.g., $CO_2$ and $H_2O$ are removed from the reactor bed) is designed to similar specification.

Forward flow inlet area ($A_{PFI}$) is 8% of reactor flow area. Reverse flow outlet area ($A_{PRO}$) is 11.7% of reactor flow area. For this reactor diameter, minimum and maximum valve sizes may be 15 cm (5.9 in) ($D_{PMIN}$) and 60 cm (24 in) ($D_{PMAX}$), respectively. Actual valve sizes are 33.0 cm (13 in) and 45.7 cm (18 in), for the forward flow inlet and reverse flow outlet valves, respectively. Valve lift is 18.7% and 18.8% of poppet diameter for the forward flow inlet and reverse flow outlet valves, respectively.

Example 3

Pyrolysis Reactor

The configuration of Example 2 is further specified in terms of the spacing between valves and the gap between the valves and the reactor bed materials. This example design corresponds roughly to the drawing of FIG. 2. In this example, the total gap between the valve-head and the bed ($G_C$) is 25 cm (10 in). With this gap, the ratio of open flow path volume to packed flow path volume is 0.41. Entry flow around the 33.0 cm (13 in) (forward inlet) valve was measured. The inlet valve is open with a gap ($G_O$) of 18.8 cm (7.4 in), which is 58% of poppet diameter. The reverse flow outlet valve in this example (shown in closed position) operates with a gap ($G_O$) that is 36% of poppet diameter. Computational Fluid Dynamics (CFD) applied to this reactor indicated that flow rate and pressure requirements were met by the design, while also providing sufficient distribution of the flow for the reaction to occur equally across the entire reactor. An acceptable level of flow uniformity was also achieved, notwithstanding a relatively small distance between poppet valve and reactor bed. CFD also showed that the spacing between valves within the forward flow inlet rows which was 177% of valve diameter was large enough to avoid interferences between the valves that can exaggerate velocity non-uniformity, but not large enough to degrade distribution, particularly when considering only a fraction of valves are used at any one time. Spacing was sufficiently close to provide sufficient valves and flow area to yield desired pressure drop.

TABLE 1

Dimensions for Examples 1 and 2

| BED DIMENSIONS | | PSR (Example 1) | | Pyrolysis (Example 2) | |
|---|---|---|---|---|---|
| Bed Height | m | 0.2413 | | 1.219 | |
| Bed Diameter | m | 0.0635 | | 3.658 | |
| Cross-Sectional Area | m² | 3.17E–03 | | 10.51 | |
| VALVE DIMENSIONS | | Inlet | Exhaust | Inlet | Exhaust |
| Diameter | m | 0.0381 | 0.0254 | 0.330 | 0.457 |
| Area | m² | 1.14E–03 | 5.07E–04 | 0.09 | 0.16 |
| Number | # | 1 | 1 | 13 | 10 |
| Valve Lift | m | 2.20E–03 | 2.20E–03 | 0.062 | 0.086 |
| Flow Area (per Valve) | m² | 2.63E–04 | 1.76E–04 | 0.064 | 0.123 |
| Stream Flow Area (total) | m² | 2.63E–04 | 1.76E–04 | 0.835 | 1.231 |
| Valve Gap Closed ($G_C$) | m | | | 0.250 | 0.250 |
| Valve Gap Open ($G_O$) | m | | | 0.188 | 0.164 |
| Valve Spacing | | | | | |
| Between Rows | m | | | 0.635 | 0.635 |
| Between Valves | m | | | 0.584 | 0.660 |
| FLOW PATH PROPERTIES | | | | | |
| Open flow path volume | m³ | | | 5.26 | |
| Packed flow path volume | m³ | | | 12.81 | |
| STREAM PROPERTIES | | Regen | Reform | Regen | Pyrolysis |
| Feed | | | | | |
| Total Flowrate | kg/s | 0.01021 | 0.00218 | 37.674 | 16.429 |
| Fuel Flowrate | kg/s | 0.01017 | N/A | 0.5625 | N/A |
| Air Flowrate | kg/s | 0.0004 | N/A | 37.111 | N/A |
| Temperature | ° C. | 250 | 150 | 100 | 100 |
| Pressure | bara | 1.3 | 17 | 1.33 | 1.33 |
| Outlet | | | | | |
| Flowrate | kg/s | 0.01021 | 0.00218 | 38.44 | 14.899 |
| Temperature | ° C. | 390 | 270 | 265 | 354 |
| Pressure | bar | 1.05 | 17 | 1.158 | 1.158 |

In other embodiments, the reactor may include other configurations in addition to the head and reactor body or shell, noted above. For instance, the reactor body may be formed of one unit or different components, which form a reaction zone within the reactor body. Further, the one or more poppet valve assemblies may be coupled to the directly to reactor body or may be coupled to other conduits that are coupled directly to the reactor body or the head. Accordingly, in one embodiment, a reactor may include a reactor body, wherein the reactor body forms a reaction zone within the reactor body; a packing material disposed within the reaction zone; and one or more poppet valve assemblies coupled to the reactor body and in flow communication with the reaction zone and controlling fluid flow between a location external to the reactor body and within the reaction zone. The reactor body may be one unit, different components, or may be a head and a shell configuration. The operation of the reactor and the poppet valve assemblies may operate as discussed above.

The packing material may include different types of packing material, such as pebbles or engineered packing material, as noted above. If the packing material is engineering packing material it may include material provided in a specific configuration, such as a honeycomb, ceramic foams or the like. These engineered packing materials have a higher geometric surface area ($a_r$), as compared to other bed structures. The use of this type of packing allows for higher gas hourly space velocity, higher volumetric reactor productivity, higher thermal efficiency, and smaller, more economical reactors.

Further, a computing device may be utilized to model the configuration or operation of the present techniques. The present system and methodology is, in a preferred embodiment thereof, may be implemented as a set of instructions or software based system resident on a computing device. As would be apparent to one of skill in the art, the present invention need not, however, be limited thereto and the teachings may be implemented in a variety of other ways including via hardware, such as special purpose chips such as ASICs and/or digital signal processor (DSP) chips and/or programmable logic arrays. The processor may further be coupled to input/output devices, such as a mouse and keyboard, and a display device, such as a monitor.

The instructions may be stored in memory or other suitable location and may be executable by the processor. The instructions may be executed to generate model results based on one or more poppet valve assemblies coupled to a reactor body and in flow communication with a reaction zone, wherein the one or more poppet valve assemblies control fluid flow between a location external to the reactor body and within the reaction zone; and store the model results in memory or other suitable media. Further, the instructions may be executed to generate model results based on spacing of the one or more poppet valve assemblies coupled to a reactor body.

Other embodiments may include:
1. A reactor comprising:
  a) a reactor body;
  b) a first head engaged with said reactor body;
  c) a first conduit extending from outside said head to at least partially through said head; and
  d) a first valve in flow communication with said first conduit controlling fluid flow along a flow path extending from the first valve and through the reactor body.
2. The reactor of paragraph 1 further comprising at least one of:
  e) a second head engaged with said reactor body;
  f) a second conduit extending from outside the first head or the second head to at least partially through said respective head; and
  g) a second valve in flow communication with said second conduit controlling fluid flow along the flow path including a portion extended from the reactor body to the second valve.
3. The reactor of paragraph 2, wherein said first valve has a substantially open position when fluid flow in the flow path is in a first flow direction and a substantially closed position when fluid flow in the flow path is in a second, opposite flow direction.
4. The reactor of paragraph 3 having a first valve pair on opposite sides of at least a portion of the flow path, wherein said first valve and second valve are each in a substantially open position when fluid flow in the flow path is in a first flow direction and a substantially closed position when fluid flow in the flow path is in a second, opposite flow direction.
5. The reactor of paragraph 4 further comprising:
  h) a third conduit extending from outside the first head or the second head to at least partially through said respective head;
  i) a third valve in flow communication with said third conduit controlling fluid flow along the flow path including a portion extended from the reactor body to the third valve;
  j) a fourth conduit extending from outside the first head or the second head to at least partially through said respective head; and
  k) a fourth valve in flow communication with said second conduit controlling fluid flow along the flow path including a portion extended from the reactor body to the fourth valve.
6. The reactor of paragraph 5, having a second valve pair comprising said third valve and said fourth valve on opposite sides of at least a portion of the flow path, controlling flow in the second, opposite flow direction wherein the third valve and the fourth valve are each in a substantially closed position when the fluid flow in the flow path is in the first flow direction and in a substantially open position when fluid flow in the flow path is in the second, opposite flow direction.
7. The reactor of paragraph 6, wherein the reactor is an asymmetric reverse flow reactor.
8. The reactor of paragraph 6 further comprising one or more additional valves, each in flow communication with one of said first, second, third, or fourth conduits via an additional conduit extending at least partially through said additional conduit's respective head, operating in phase with any other valves in fluid communication with said additional conduit and controlling fluid flow along the flow path including a portion extended from the reactor body to the respective valve.
9. The reactor of paragraph 2, wherein the reactor body comprises a reactor bed, and the volume of the flow path consists of i) a packed flow path volume within a solids-fluids contact portion of the reactor bed and ii) an open flow path volume between the valve(s) and the reactor bed, as well as any open flow portion within the reactor bed.
10. The reactor of paragraph 9, wherein said packed flow volume comprises all volume in the reactor bed that is at a distance less than 2 cm from a solids-fluid contact surface.
11. The reactor of paragraph 9, wherein said solids-fluids contact portion of the reactor bed has a wetted area greater than 0.5 $cm^2/cm^3$ in all regions of said portion of the reactor bed.
12. The reactor of paragraph 9, wherein the ratio of the open flow path volume to packed flow path volume is less than 1.
13. The reactor of paragraph 9, wherein the ratio of the open flow path volume to packed flow path volume is less than 0.5.
14. The reactor of paragraph 9, wherein the reactor bed comprises a fixed bed core comprising solid material capable of heat exchange.
15. The reactor of paragraph 9, wherein at least one of said valves is a poppet valve comprising a disk element connected to a valve stem element.

16. The reactor of paragraph 15, wherein the poppet valve disk element has a surface substantially parallel to and facing the proximal reactor bed surface.

17. The reactor of paragraph 16, wherein the poppet valve opens toward the reactor bed.

18. The reactor of paragraph 16, wherein the poppet valve opens away from the reactor bed.

19. The reactor of paragraph 16, wherein the distance during operation between the poppet valve disk element flat surface in the fully open position and the reactor bed surface is between 5% and 200% of the disk element diameter.

20. The reactor of paragraph 16, wherein the distance during operation between the poppet valve disk element flat surface in the fully open position and the reactor bed surface is between 20% and 80% of the disk element diameter.

21. The reactor of paragraph 15, wherein said poppet valve stem element extends to a location outside said head.

22. The reactor of paragraph 2, wherein each valve is associated with an externally accessible valve seat that fits within its respective inlet to the reactor body and/or outlet from the reactor body and is sealed to the head.

23. The reactor of paragraph 22, wherein the valve seat is attached to the head via one of a rotatably locking mechanism, thread-in seats, and pressed-in seats.

24. The reactor of paragraph 21, which further comprises a valve stem seal associated with the valve stem.

25. The reactor of paragraph 24, wherein the valve stem seal is a rod packing.

26. The reactor of paragraph 15, wherein the poppet valve comprises a linearly actuatable valve stem engageable with an actuator to open and close the valve by imparting linear motion.

27. The reactor of paragraph 26, wherein the actuator is at least one of pneumatically actuated, hydraulically actuated, and electromagnetically actuated.

28. The reactor of paragraph 26, wherein the actuator is camshaft actuated.

29. The reactor of paragraph 26, wherein a common actuator controls linearly aligned plural valves common to a particular fluid flow stream.

30. The reactor of paragraph 15, wherein circular poppet valves associated with a particular head are substantially circular, uniform in diameter and spaced center-to-center by 120% to 400% of the average poppet disk element diameter.

31. The reactor of paragraph 15, wherein circular poppet valves associated with a particular head are substantially circular, uniform in diameter and spaced center-to-center by 140% to 200% of the average poppet disk element diameter.

32. The reactor of paragraph 15 which provides at least one of: i) a valve pressure drop as fluid flows through a valve of from 1% to 100% of the reactor internal pressure drop; ii) a ratio of total stream poppet valve flow area for one of an inlet stream and an outlet stream to reactor flow area ranging from 1% to 30%; iii) a poppet valve diameter between minimum value ($D_{PMIN}$) [inches]=0.1484+0.4876*$D_B$ [feet], where $D_B$ is flow area diameter in feet, and maximum value ($D_{PMAX}$) [inches]=1.6113+1.8657*$D_B$ [feet], where $D_B$ is flow area diameter in feet; iv) $L_P/D_P$, (the ratio of valve lift to poppet diameter) ranges between 3% and 25%; and v) valve lift times of at least 50 milliseconds.

33. The reactor of paragraph 15 which provides at least one of: i) a valve pressure drop as fluid flows through a valve of from 5% to 20% of the reactor internal pressure drop; ii) a ratio of total stream poppet valve flow area for one of an inlet stream and an outlet stream to reactor flow area ranging from 2% to 20%; iii) a poppet valve diameter between minimum value ($D_{PMIN}$) [inches]=0.1484+0.4876*$D_B$ [feet], where $D_B$ is flow area diameter in feet, and maximum value ($D_{PMAX}$) [inches]=1.6113+1.8657*$D_B$ [feet], where $D_B$ is flow area diameter in feet; iv) $L_P/D_P$, (the ratio of valve lift to poppet diameter) ranges between 5% and 20%; and v) valve lift times between 100 and 500 milliseconds.

34. A reactor comprising:
    a) a reactor body partially enclosing a reaction and/or heat exchange region comprising two substantially opposing open ends;
    b) a first head capping one end of the reactor body;
    c) a second head capping the opposing end of the reactor body;
    d) a fixed bed comprising a region proximal to the first head, a region proximal to the second head and a central region disposed therebetween, which fixed bed is disposed within the reactor body and comprises solid material capable of promoting heat exchange and/or reaction of a gas stream;
    e) at least one gas stream inlet associated with the first head opening a pathway through the first head and into the reactor body and at least one gas stream outlet associated with the second head opening a pathway from the reactor body and through the second head;
    f) at least one inlet poppet valve controlling the gas stream inlet and integrated with the head associated with the inlet, the inlet poppet valve comprising a linearly actuatable valve stem;
    g) at least one outlet poppet valve controlling the gas stream outlet and integrated with the head associated with the outlet, the outlet poppet valve comprising a linearly actuatable valve stem; and
    h) at least one actuator engageable with the linearly actuatable valve stem of f) and/or g) providing valve opening and closing by imparting linear motion to the poppet valve to allow gases to pass from outside the reactor to inside the reactor body, and from inside the reactor body to outside the reactor so as to provide changeable flow operation.

35. The reactor of paragraph 34 which further comprises i) at least one gas stream inlet is associated with the second head opening a pathway through the second head and the reactor body and at least one gas stream outlet associated with the first head opening a pathway through the reactor body and the first head, with associated inlet poppet valve(s) or other inlet flow control means, outlet poppet valve(s) and actuator(s) analogous to f), g) and h).

36. A process for rapid stream-switching of at least two streams in a reverse-flow reactor comprising a reactor body partially enclosing a reaction and/or heat exchange region comprising two substantially opposing open ends with a first head capping one end of the reactor body, a second head capping the opposing end of the reactor body, a fixed bed disposed within the reactor body comprising solid material capable of promoting heat exchange and/or reaction of a gas stream, which comprises:
    i) introducing from one or more inlet gas sources at least one first gas stream to at least one gas stream inlet associated with the first head through the first head and into the reactor body and withdrawing a treated first gas stream from the reactor body and through the second head to at least one gas stream outlet associated with the second head; wherein said introducing and withdrawing are controlled respectively by at least one intake poppet valve located in the first head and at least one exhaust poppet valve located in the second head; and
    ii) introducing from one or more inlet gas sources at least one second gas stream to at least one gas stream inlet associated with the second head through the second head and into the reactor body and withdrawing a treated second gas stream from the reactor body and through the first head to at least one gas stream outlet associated with the first head, wherein said introducing and withdrawing are controlled respectively by at least one intake poppet valve or other intake flow control means located in the second head and at least one exhaust poppet valve located in the first head.

37. A reactor comprising:
   a) a reactor body, wherein the reactor body forms a reaction zone within the reactor body;
   b) a packing material disposed within the reaction zone;
   c) one or more poppet valve assemblies coupled to the reactor body and in flow communication with the reaction zone and controlling fluid flow between a location external to the reactor body and within the reaction zone.

38. The reactor of paragraph 37, wherein the reactor body comprises a head and a shell coupled together to form the reaction zone; and wherein the one or more poppet valve assembly are coupled to the head.

39. The reactor of paragraph 38, wherein the one or more poppet valve assemblies comprise:
   i) a first conduit extending from outside the head to at least partially through the head; and
   ii) a first valve in flow communication with the first conduit controlling fluid flow along a flow path extending from the first valve and through the reactor body.

40. The reactor of paragraph 39, wherein the first valve has a substantially open position when fluid flow in the flow path is in a first flow direction and a substantially closed position when fluid flow in the flow path is in a second, opposite flow direction.

41. A computing device, comprising:
a processor;
a memory coupled to the processor; and
instructions provided to the memory, wherein the instructions are executable by the processor to:
generate model results based on one or more poppet valve assemblies coupled to a reactor body and in flow communication with a reaction zone, wherein the one or more poppet valve assemblies control fluid flow between a location external to the reactor body and within the reaction zone;
store the model results.

42. The computing device of paragraph 41, wherein the model results are based on spacing of the one or more poppet valve assemblies coupled to a reactor body.

43. The reactor of paragraph 37, wherein the reactor is an asymmetric reverse flow reactor.

44. The reactor of paragraph 37, wherein the packing material is a honeycomb packing material.

Other embodiments may include:

1A. A reactor comprising:
   a) a reactor body;
   b) a first head engaged with said reactor body;
   c) a first conduit extending from outside said head to at least partially through said head; and
   d) a first valve in flow communication with said first conduit controlling fluid flow along a flow path extending from the first valve and through the reactor body.

2A. The reactor of paragraph 2A further comprising at least one of:
   e) a second head engaged with said reactor body;
   f) a second conduit extending from outside the first head or the second head to at least partially through said respective head; and
   g) a second valve in flow communication with said second conduit controlling fluid flow along the flow path including a portion extended from the reactor body to the second valve.

3A. The reactor of any of the preceding paragraphs, wherein said first valve has a substantially open position when fluid flow in the flow path is in a first flow direction and a substantially closed position when fluid flow in the flow path is in a second, opposite flow direction.

4A. The reactor of any of the preceding paragraphs 2A to 3A, having a first valve pair on opposite sides of at least a portion of the flow path, wherein said first valve and second valve are each in a substantially open position when fluid flow in the flow path is in a first flow direction and a substantially closed position when fluid flow in the flow path is in a second, opposite flow direction.

5A. The reactor of any of the preceding paragraphs 2A to 4A further comprising: h) a third conduit extending from outside the first head or the second head to at least partially through said respective head; i) a third valve in flow communication with said third conduit controlling fluid flow along the flow path including a portion extended from the reactor body to the third valve; j) a fourth conduit extending from outside the first head or the second head to at least partially through said respective head; and k) a fourth valve in flow communication with said second conduit controlling fluid flow along the flow path including a portion extended from the reactor body to the fourth valve.

6A. The reactor of paragraph 5A, having a second valve pair comprising said third valve and said fourth valve on opposite sides of at least a portion of the flow path, controlling flow in the second, opposite flow direction wherein the third valve and the fourth valve are each in a substantially closed position when the fluid flow in the flow path is in the first flow direction and in a substantially open position when fluid flow in the flow path is in the second, opposite flow direction.

7A. The reactor of any of the preceding paragraphs, wherein the reactor is an asymmetric reverse flow reactor.

8A. The reactor of any of the preceding paragraphs 5A and 6A, further comprising one or more additional valves, each in flow communication with one of said first, second, third, or fourth conduits via an additional conduit extending at least partially through said additional conduit's respective head, operating in phase with any other valves in fluid communication with said additional conduit and controlling fluid flow along the flow path including a portion extended from the reactor body to the respective valve.

9A. The reactor of any of the preceding paragraphs, wherein the reactor body comprises a reactor bed, and the volume of the flow path consists of i) a packed flow path volume within a solids-fluids contact portion of the reactor bed and ii) an open flow path volume between the valve(s) and the reactor bed, as well as any open flow portion within the reactor bed.

10A. The reactor of paragraph 9A, wherein said packed flow volume comprises all volume in the reactor bed that is at a distance less than 2 cm from a solids-fluid contact surface.

11A. The reactor of paragraph 9A, wherein said solids-fluids contact portion of the reactor bed has a wetted area greater than 0.5 $cm^2/cm^3$ in all regions of said portion of the reactor bed.

12A. The reactor of paragraph 9A, wherein the ratio of the open flow path volume to packed flow path volume is less than 1.

13A. The reactor of paragraph 9A, wherein the ratio of the open flow path volume to packed flow path volume is less than 0.5.

14A. The reactor of paragraph 9A, wherein the reactor bed comprises a fixed bed core comprising solid material capable of heat exchange.

15A. The reactor of paragraph 9A, wherein at least one of said valves is a poppet valve comprising a disk element connected to a valve stem element.

16A. The reactor of paragraph 15A, wherein the poppet valve disk element has a surface substantially parallel to and facing the proximal reactor bed surface.

17A. The reactor of paragraph 15A or 16A, wherein the poppet valve opens toward the reactor bed.

18A. The reactor of paragraph 15A or 16A, wherein the poppet valve opens away from the reactor bed.

19A. The reactor of paragraph 15A, 16A, 17A, or 18A, wherein the distance during operation between the poppet valve disk element flat surface in the fully open position and the reactor bed surface is between 5% and 200% of the disk element diameter.

20A. The reactor of paragraphs 15A, 16A, 17A, or 18A, wherein the distance during operation between the poppet valve disk element flat surface in the fully open position and the reactor bed surface is between 20% and 80% of the disk element diameter.

21A. The reactor of paragraphs 15A, 16A, 17A, or 18A, wherein said poppet valve stem element extends to a location outside said head.

22A. The reactor of any of the preceding paragraphs, wherein each valve is associated with an externally accessible valve seat that fits within its respective inlet to the reactor body and/or outlet from the reactor body and is sealed to the head.

23A. The reactor of paragraph 22A, wherein the valve seat is attached to the head via one of a rotatable locking mechanism, thread-in seats, and pressed-in seats.

24A. The reactor of paragraph 21A, which further comprises a valve stem seal associated with the valve stem.

25A. The reactor of paragraph 24A, wherein the valve stem seal is a rod packing.

26A. The reactor of paragraph 15A, wherein the poppet valve comprises a linearly actuatable valve stem engageable with an actuator to open and close the valve by imparting linear motion.

27A. The reactor of paragraph 26A, wherein the actuator is at least one of pneumatically actuated, hydraulically actuated, and electromagnetically actuated.

28A. The reactor of paragraph 26A, wherein the actuator is camshaft actuated.

29A. The reactor of paragraph 26A, wherein a common actuator controls linearly aligned plural valves common to a particular fluid flow stream.

30A. The reactor of paragraph 15A, wherein circular poppet valves associated with a particular head are substantially circular, uniform in diameter and spaced center-to-center by 120% to 400% of the average poppet disk element diameter.

31A. The reactor of paragraph 15A, wherein circular poppet valves associated with a particular head are substantially circular, uniform in diameter and spaced center-to-center by 140% to 200% of the average poppet disk element diameter.

32A. The reactor of paragraph 15A which provides at least one of: i) a valve pressure drop as fluid flows through a valve of from 1% to 100% of the reactor internal pressure drop; ii) a ratio of total stream poppet valve flow area for one of an inlet stream and an outlet stream to reactor flow area ranging from 1% to 30%; iii) a poppet valve diameter between minimum value ($D_{PMIN}$) [inches]=$0.1484+0.4876*D_B$ [feet], where $D_B$ is flow area diameter in feet, and maximum value ($D_{PMAX}$) [inches]=$1.6113+1.8657*D_B$ [feet], where $D_B$ is flow area diameter in feet; iv) $L_P/D_P$, (the ratio of valve lift to poppet diameter) ranges between 3% and 25%; and v) valve lift times of at least 50 milliseconds.

33A. The reactor of paragraph 15A which provides at least one of: i) a valve pressure drop as fluid flows through a valve of from 5% to 20% of the reactor internal pressure drop; ii) a ratio of total stream poppet valve flow area for one of an inlet stream and an outlet stream to reactor flow area ranging from 2% to 20%; iii) a poppet valve diameter between minimum value ($D_{PMIN}$) [inches]=$0.1484+0.4876*D_B$ [feet], where $D_B$ is flow area diameter in feet, and maximum value ($D_{PMAX}$) [inches]=$1.6113+1.8657*D_B$ [feet], where $D_B$ is flow area diameter in feet; iv) $L_P/D_P$, (the ratio of valve lift to poppet diameter) ranges between 5% and 20%; and v) valve lift times between 100 and 500 milliseconds.

34A. The reactor of any of the preceding paragraphs which is a reverse-flow reactor used for at least one of steam reforming, dry ($CO_2$) reforming, pyrolysis, catalytic cracking, dehydrogenation, and dehydration.

35A. The reactor of paragraph 34A, wherein pyrolysis is selected from steam cracking, hydropyrolysis, and non-hydrocarbon cracking.

36A. The reactor of paragraph 35A, wherein steam cracking includes at least one of ethane cracking, naphtha cracking, and gas oil cracking.

37A. The reactor of paragraph 35A, wherein hydropyrolysis is selected from methane hydropyrolysis to acetylene and heavy feed hydropyrolysis to acetylene.

38A. The reactor of paragraph 35A, wherein non-hydrocarbon cracking is selected from hydrogen sulfide pyrolysis to hydrogen and sulfur.

39A. The reactor of paragraph 34A, wherein dehydrogenation is selected from alkane dehydrogenation and alkyl-aromatic dehydrogenation.

40A. The reactor of paragraph 34A, wherein dehydration is selected from methanol dehydration and ethanol dehydration.

41A. A reactor comprising:
 a) a reactor body, wherein the reactor body forms a reaction zone within the reactor body;
 b) a packing material disposed within the reaction zone;
 c) one or more poppet valve assemblies coupled to the reactor body and in flow communication with the reaction zone and controlling fluid flow between a location external to the reactor body and within the reaction zone.

42A. The reactor of paragraph 41A, wherein the reactor body comprises a head and a shell coupled together to form the reaction zone; and wherein the one or more poppet valve assembly are coupled to the head.

43A. The reactor of paragraph 42A, wherein the one or more poppet valve assemblies comprise:
 i) a first conduit extending from outside the head to at least partially through the head; and
 ii) a first valve in flow communication with the first conduit controlling fluid flow along a flow path extending from the first valve and through the reactor body.

44A. The reactor of paragraph 43A, wherein the first valve has a substantially open position when fluid flow in the flow path is in a first flow direction and a substantially closed position when fluid flow in the flow path is in a second, opposite flow direction.

45A. A computing device, comprising:
 a processor;
 a memory coupled to the processor; and
 instructions provided to the memory, wherein the instructions are executable by the processor to:
  generate model results based on at least spacing between one or more poppet valve assemblies coupled to a reactor body and in flow communication with a reaction zone, wherein the one or more poppet valve control fluid flow between a location external to the reactor body and within the reaction zone;
  store the model results.

46A. The computing device of paragraph 45A, wherein the model results are based on spacing of the one or more poppet valve assemblies coupled to a reactor body.

47A. The reactor of paragraph 41A, wherein the reactor is an asymmetric reverse flow reactor.

48A. The reactor of paragraph 41A, wherein the packing material is a honeycomb packing material.

49A. The reactor of paragraph 37A, wherein the acetylene is converted to ethylene.

As may be appreciated, in an alternative embodiment, the reactor of paragraph 15 and 15A may provide at least one of: i) a valve pressure drop as fluid flows through a valve of from 5% to 20% of the reactor internal pressure drop; ii) a ratio of total stream poppet valve flow area for one of an inlet stream and an outlet stream to reactor flow area ranging from 2% to 20%; iii) a poppet valve diameter between minimum value ($D_{PMIN}$) [inches]=0.1484+0.4876*$D_B$ [feet], where $D_B$ is flow area diameter in feet, and maximum value ($D_{PMAX}$) [inches]=1.6113+2.858*$D_B$ [feet], where $D_B$ is flow area diameter in feet; iv) $L_P/D_P$, (the ratio of valve lift to poppet diameter) ranges between 5% and 20%; and v) valve lift times between 100 and 500 milliseconds.

Although the invention has been described in detail herein, the skilled practitioner will recognize other embodiments of the invention that are within the scope of the claims.

What is claimed is:

1. A computing device for modeling a reverse-flow reactor, wherein the reactor comprises:
   a) a reverse-flow reactor having a reactor body;
   b) a first head engaged with said reactor body;
   c) a first conduit extending from outside said head to at least partially through said head;
   d) a first valve in flow communication with said first conduit controlling fluid flow along a flow path extending from the first valve and through the reactor body; wherein said first valve has a substantially open position when fluid flow in the flow path is in a first flow direction and a substantially closed position when fluid flow in the flow path is in a second, opposite flow direction;
   e) an optional second head engaged with said reactor body;
   f) a second conduit extending from outside the first head or the second head to at least partially through said respective head; and
   g) a second valve in flow communication with said second conduit controlling fluid flow along the flow path including a portion extended from the reactor body to the second valve, wherein the first and second valves are each in a substantially open position when fluid flow in the flow path is in a first flow direction and a substantially closed position when fluid flow in the flow path is in a second, opposite flow direction;
   h) a third conduit extending from outside the first head or the second head to at least partially through said respective head;
   i) a third valve in flow communication with said third conduit controlling fluid flow along the flow path including a portion extended from the reactor body to the third valve;
   j) a fourth conduit extending from outside the first head or the second head to at least partially through said respective head; and
   k) a fourth valve in flow communication with said fourth conduit controlling fluid flow along the flow path including a portion extended from the reactor body to the fourth valve;
   the computing device comprising:
   a processor;
   a memory coupled to the processor; and
   instructions provided to the memory, wherein the instructions are executable by the processor to:
      (i) generate model results based on the first and second valves, wherein first and second valves control fluid flow between first and second locations, the first location being external to the reactor body and the second location being within the reaction zone; and
      (ii) store the model results.

2. The computing device of claim 1, wherein the model results are further based on spacing of the first and second valves proximate to the reactor body.

3. The computing device of claim 1, wherein (i) the first and second valves constitute a first valve pair, the first and second valves being located on opposite sides of at least a portion of the flow path, (ii) the third and fourth valves constitute a second valve pair, the third and fourth valves being located on opposite sides of at least a portion of the flow path, (iii) the second valve pair controls flow along the flow path in a second direction, the second direction being substantially opposite to the first flow direction, and (iv) wherein the third and fourth valves are each in a substantially closed position when the fluid flow in the flow path is in the first flow direction and in a substantially open position when fluid flow in the flow path is in the second flow direction.

4. The computing device of claim 1, further comprising one or more additional valves, each in flow communication with one of said first, second, third, or fourth conduits via an additional conduit extending at least partially through said additional conduit's respective head, operating in phase with any other valves in fluid communication with said additional conduit and controlling fluid flow along the flow path including a portion extended from the reactor body to the respective valve.

5. The computing device of claim 1, wherein at least one of the first and second valves is a poppet valve, the poppet valve comprising a disk element connected to a valve stem element, the disk element having at least one substantially flat surface.

6. The computing device of claim 5, wherein (i) the reactor body contains at least one reactor bed, (ii) the reactor bed comprises at least one substantially flat surface, (iii) the poppet valve disk element has at least one substantially flat surface, (iv) the poppet valve's substantially flat surface is substantially parallel to and facing the reactor bed's substantially flat surface, and (v) the distance during operation between the poppet valve disk element's substantially flat surface in the fully open position and the reactor bed's substantially flat surface is between 5% and 200% of the disk element's diameter.

* * * * *